US008088615B2

(12) United States Patent
Ausserre

(10) Patent No.: US 8,088,615 B2
(45) Date of Patent: Jan. 3, 2012

(54) OPTICAL COMPONENT FOR OBSERVING A NANOMETRIC SAMPLE, SYSTEM COMPRISING SAME, ANALYSIS METHOD USING SAME, AND USES THEREOF

(76) Inventor: Dominique Ausserre, Soulitre (FR)

( * ) Notice: Subject to any disclaimer, the term of this patent is extended or adjusted under 35 U.S.C. 154(b) by 777 days.

(21) Appl. No.: 11/631,846

(22) PCT Filed: Jul. 6, 2005
(Under 37 CFR 1.47)

(86) PCT No.: PCT/FR2005/001746
§ 371 (c)(1),
(2), (4) Date: Aug. 12, 2008

(87) PCT Pub. No.: WO2006/013287
PCT Pub. Date: Feb. 9, 2006

(65) Prior Publication Data
US 2010/0062422 A1    Mar. 11, 2010

(30) Foreign Application Priority Data

Jul. 7, 2004  (FR) ...................................... 04 07517

(51) Int. Cl.
*C12Q 1/68* (2006.01)
*C12M 1/34* (2006.01)
*G01J 4/00* (2006.01)

(52) U.S. Cl. ........................... 435/287.2; 435/6; 356/369

(58) Field of Classification Search .................. 356/244, 356/246, 445, 364–369; 435/287.1, 287.2, 435/287.7, 287.9; 436/518, 146, 172, 524; 422/82.05, 82.08, 82.11; 359/280, 359; 382/128, 382/255

See application file for complete search history.

(56) References Cited

U.S. PATENT DOCUMENTS

| 5,639,671 | A  | * | 6/1997  | Bogart et al. ............... 436/518 |
| 5,962,114 | A  | * | 10/1999 | Jonza et al. ................ 428/212 |
| 6,034,775 | A  | * | 3/2000  | McFarland et al. ........... 506/12 |
| 6,312,691 | B1 | * | 11/2001 | Browning et al. ......... 424/143.1 |
| 6,493,423 | B1 | * | 12/2002 | Bisschops .................. 378/119 |
| 6,697,194 | B2 | * | 2/2004  | Kuschnereit et al. ......... 359/359 |
| 6,710,875 | B1 | * | 3/2004  | Zavislan .................... 356/364 |
| 6,718,053 | B1 | * | 4/2004  | Ellis et al. ................. 382/128 |
| 6,853,455 | B1 | * | 2/2005  | Dixon et al. ................ 356/453 |
| 6,934,068 | B2 | * | 8/2005  | Kochergin .................. 359/280 |
| 7,209,232 | B2 | * | 4/2007  | Ausserre et al. ............ 356/369 |
| 7,258,838 | B2 | * | 8/2007  | Li et al. ..................... 422/68.1 |
| 7,265,845 | B2 | * | 9/2007  | Kochergin .................. 356/445 |

* cited by examiner

*Primary Examiner* — Sang Nguyen
(74) *Attorney, Agent, or Firm* — Blank Rome LLP

(57) ABSTRACT

The invention concerns an optical component for observing a sample, which includes a substrate and at least one complex index layer of predetermined thickness, designed to show a high intensity or color contrast for optical path variations, reliefs, nanometric thicknesses and diameters when it is observed by incoherent light reflection convergent around the normal incidence under polarization extinction conditions. The upper index layer has specific surface properties providing it with selective affinity relative to at least one characteristic of the sample. An analysis system includes such a component, an analysis method using the component and uses of the method.

61 Claims, 20 Drawing Sheets

GENERAL OUTLINE OF THE SYSTEM FOR ANALYSIS BY REFLECTION

OPTICAL COMPONENT 30

GENERAL OUTLINE OF THE SYSTEM
FOR ANALYSIS BY REFLECTION

OUTLINE OF AN OPTICAL COMPONENT
ACCORDING TO THE INVENTION

| SUPPORT No. | SUBSTRATE | CHARACTERISTICS | INCIDENT ENVIRONMENT | LAYERS | THICKNESS | INDEX | THEORETICAL THICKNESS | CONDITIONS | SUPPLIERS |
|---|---|---|---|---|---|---|---|---|---|
| 2 | SILICON | 625μ THICK | AIR | MgF2 | | | | ON=30°; λ=5400 | TOFICO |
| 3 | | ORIENTATION 100 | | | | | | | |
| 4 | | | | | | | | | TOFICO |
| 5 | | | | | | | | | TOFICO |
| 6 | | | | | | | | | |
| 7 | SILICON | 625μ THICK | AIR | SiO2 | | | | ON=30°; λ=4900 | VEGATEC |
| 8 | | | | | | | | | |
| 9 | SILICON | | OIL | HfO2 (HAFNIUM) | | | | | TOFICO |
| 10 | | | | | | | | | TOFICO |
| 11 | | | | | | | | | TOFICO |
| 12 | | | | | | | | | |
| 13 | SILICON | | WATER | Y2O3 (YITRIUM) | | | | | TOFICO |
| 14 | SILICON | | | Y2O3 (YITRIUM) | | | | | TOFICO |
| 15 | SILICON | | | | | | | | TOFICO |
| 16 | | | | | | | | | TOFICO |
| 17 | | | | | | | | | |
| 18 | GLASS | FLOATED | AIR + GLASS | Cr/CrO2 | | | | | BLOSCH |

FIG. 2B

VARIOUS PROTOTYPES OF OPTICAL COMPONENTS
ACCORDING TO THE INVENTION

IMAGES SHOWING A DNA STRAND OBTAINED USING THE OPTICAL COMPONENT ACCORDING TO THE INVENTION

IMAGE OF A SUPPORTED BILAYER OBSERVED IN IMMERSION

OVERVIEW OF A MEMBRANE PROTEIN SENSOR FOR PRODUCING A BIOCHIP WITH PROTEINS

Figure 6A:
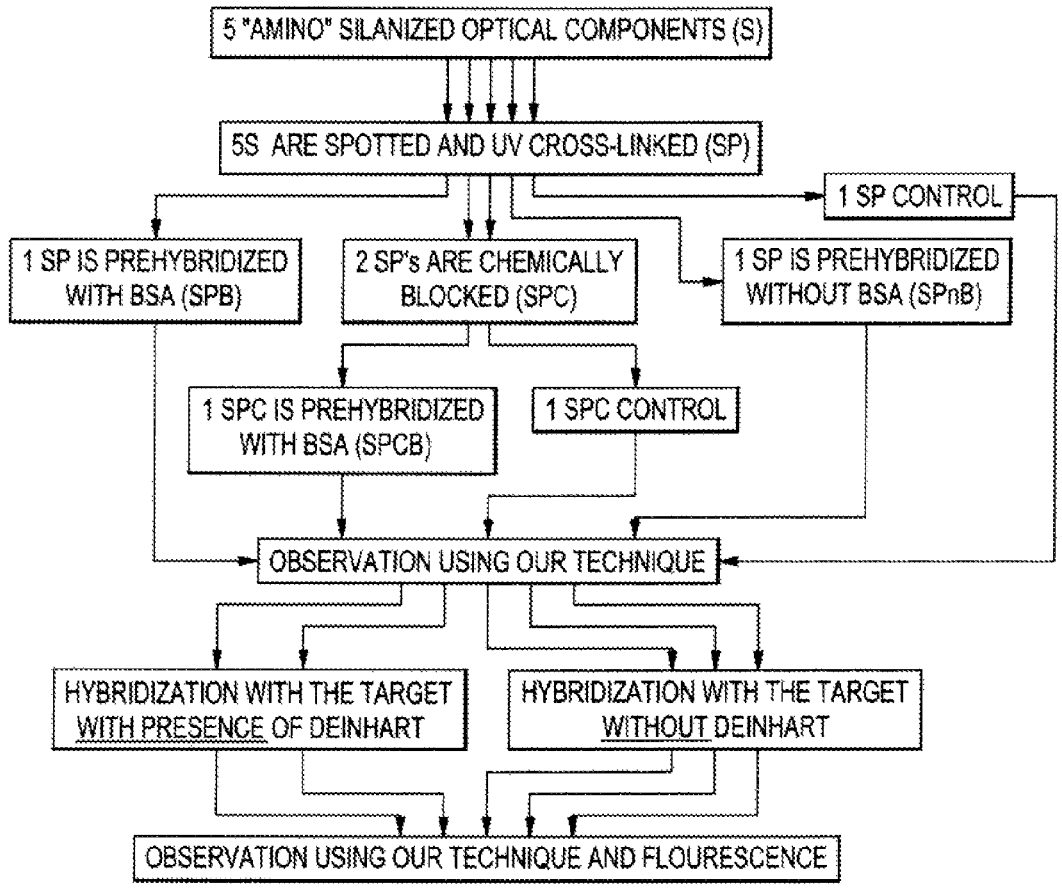
Figures 6B, 6C:
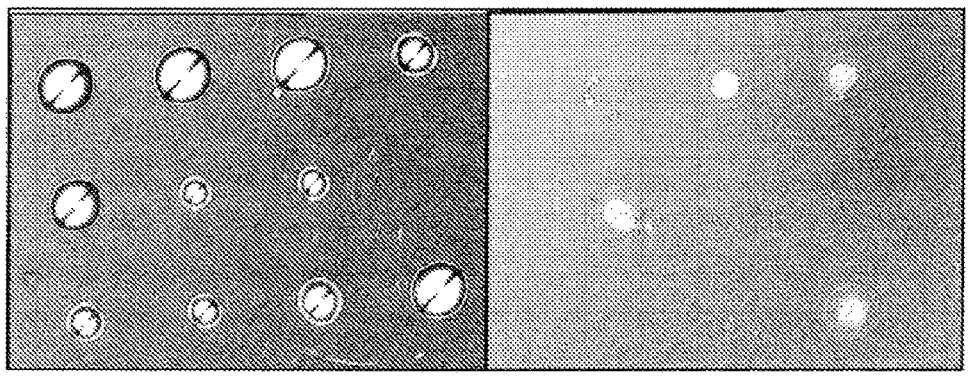
Figure 6H:
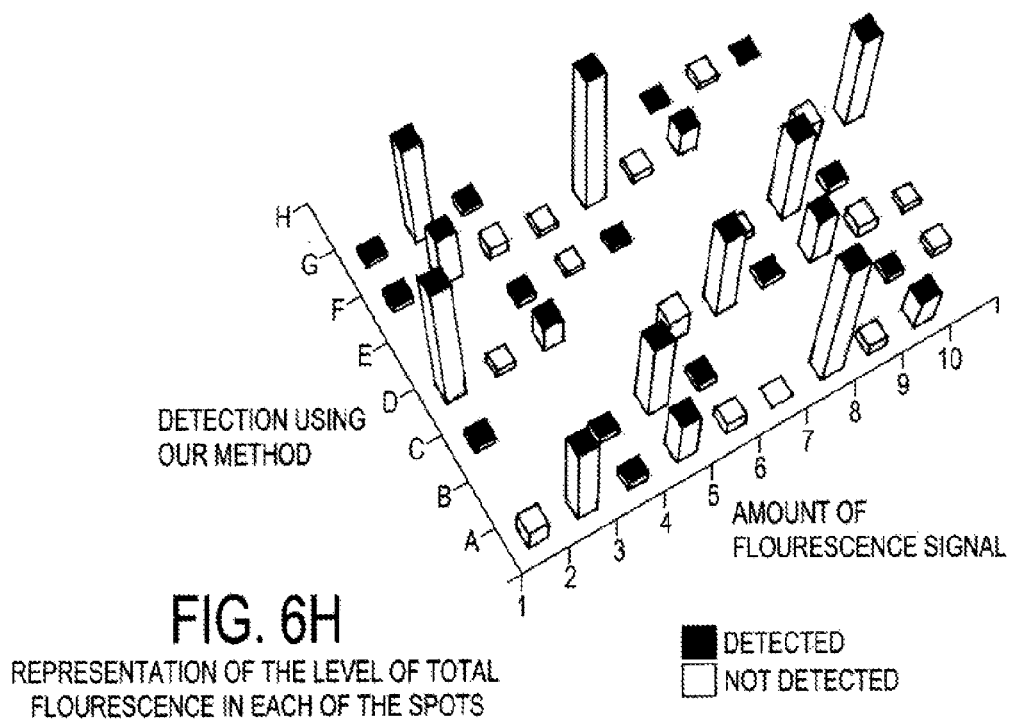
Figures 6I, 6J:
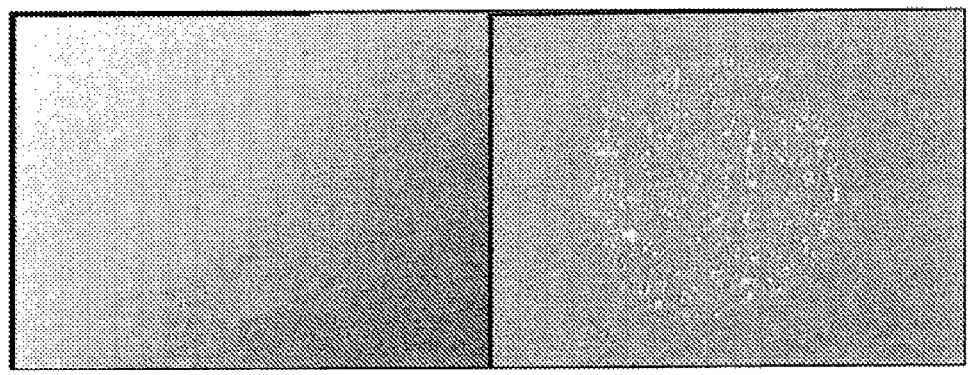

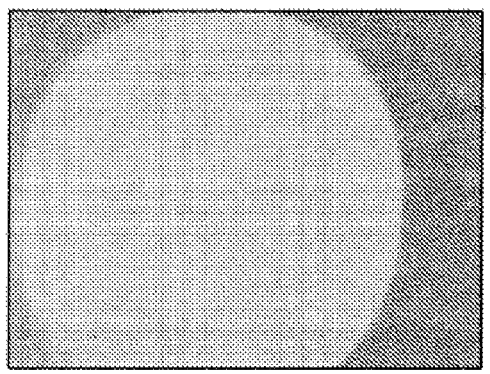
FIG. 6D
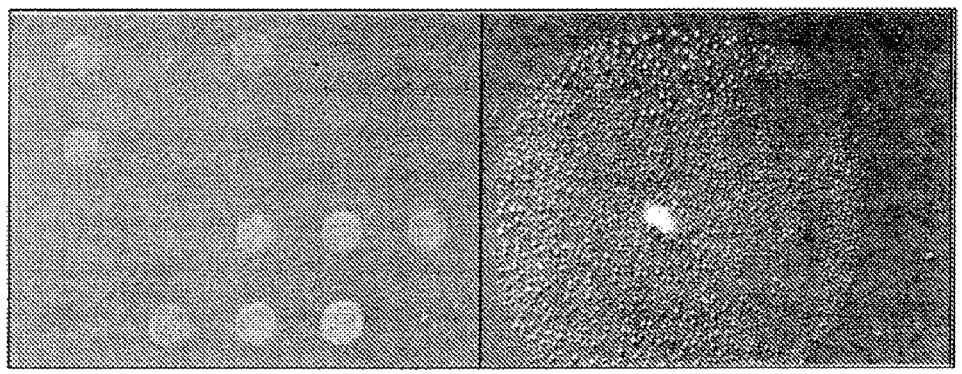
FIG. 6E
FIG. 6F
AMOUNT OF FLOURESCENCE SIGNAL
| DETECTION USING OUR METHOD | | 1 | 2 | 3 | 4 | 5 | 6 | 7 | 8 | 9 | 10 |
|---|---|---|---|---|---|---|---|---|---|---|---|
| | H | | | | | | | | | | |
| | G | 2282 | 96402 | 3868 | | | | 1542 | 5098 | 1865 | |
| | F | 6206 | 50689 | 9777 | 930 | 128209 | 6262 | 24881 | | | |
| | E | | | 1540 | 5899 | 1894 | | | | 22110 | 81795 |
| | D | 129019 | 6477 | 26294 | | | | 3439 | 80784 | 4678 | |
| | C | 1595 | | | | 22586 | 85848 | 6173 | 46861 | 9866 | 841 |
| | B | | | 3023 | 82858 | 3927 | | | | 1484 | 5297 |
| | A | 17941 | 86622 | 6228 | 48771 | 13204 | 869 | 127282 | 7030 | 25521 | |
▨ DETECTED   ☐ NOT DETECTED
FIG. 6G
SUM OF THE Cy3 AND Cy5 FLOURESCENCE SIGNALS

REPRESENTATION OF THE LEVEL OF TOTAL
FLOURESCENCE IN EACH OF THE SPOTS

■ DETECTED
□ NOT DETECTED

2D PROTEIN CRYSTALS

3D THIN PROTEIN CRYSTALS

2D POLYMER CRYSTALS (POLYETHYLENE GLYCOL 4000)

THREE-DIMENSIONAL VISUALIZATION OF THE CRYSTALIZATION OF THE
SAME POLYMER (POLYETHYLENE GLYCOL 4000) AT ROOM TEMPERATURE

INSPECTION, CONTROL, AND FOLLOW-UP OF THE
CRYSTALIZATION OF A PROTEIN GEL

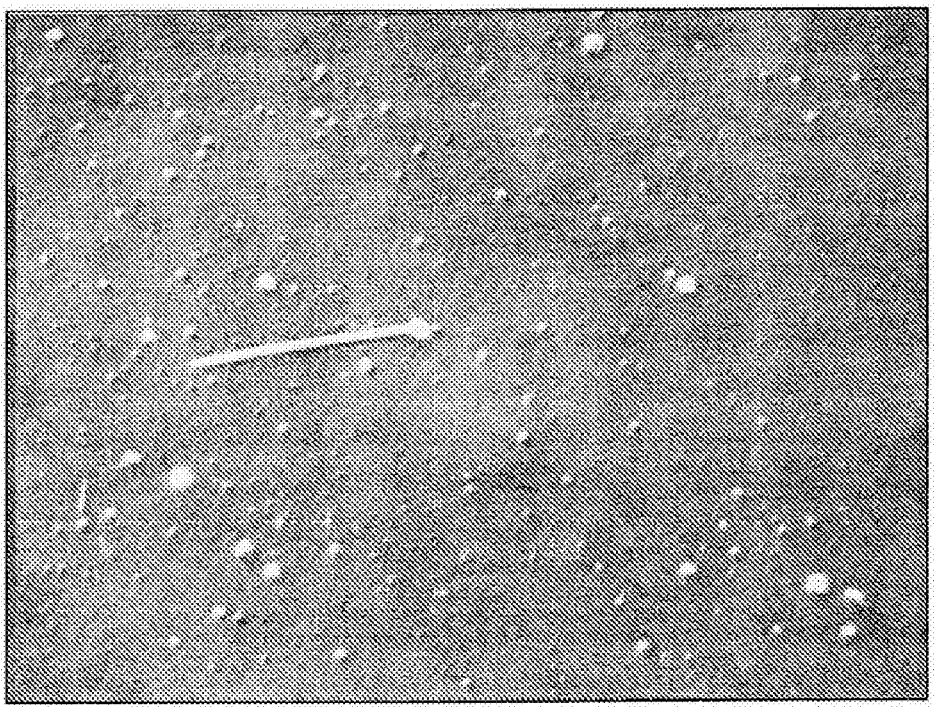
FIG. 9A ANALYSIS SYSTEM ACCORDING TO THE INVENTION FOR STUDYING AND INSPECTING NANOTUBES
FIG. 9B DETECTION OF CARBON NANOTUBES WITH RARE SHAPES

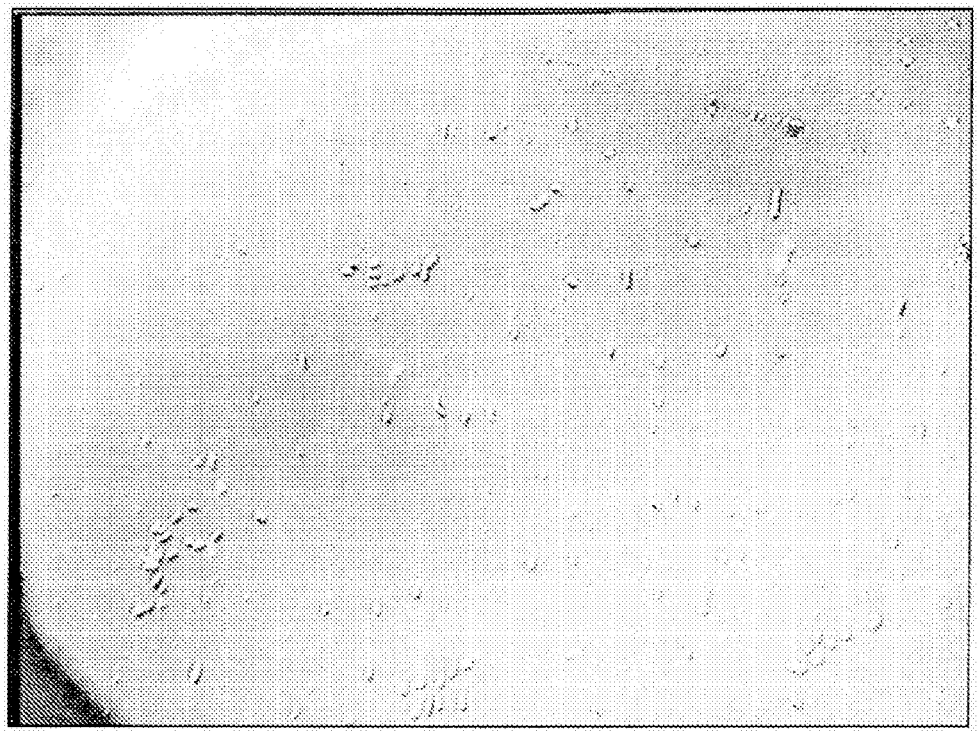
FIG. 10 FOLLOW-UP OF THE GROWTH OF A BACTERIAL POPULATION
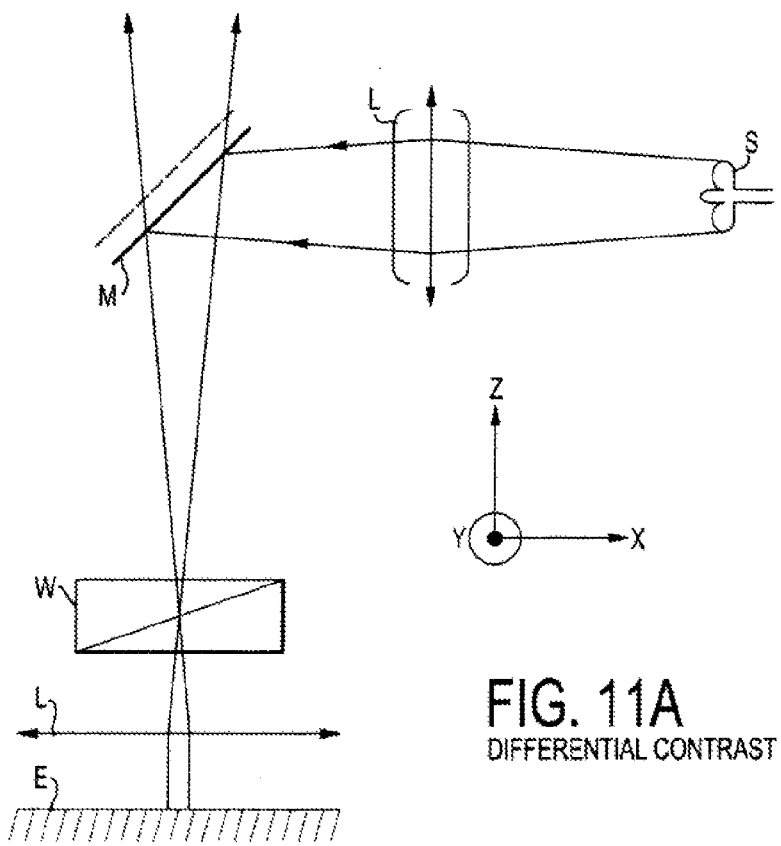
FIG. 11A
DIFFERENTIAL CONTRAST DEVICE

FIG. 11B

| | A POLARIZER P PREFERABLY ACCORDING TO Y | A COMPENSATOR | AN ORTHOGONAL ANALYZER A WITH P | AN ADJUSTABLE α/4 PLATE OR ONE SUITABLY ADJUSTED |
|---|---|---|---|---|
| CONFIGURATION 1 WITH TWO LINEAR POLARIZERS | BETWEEN S AND L OR BETWEEN L AND M OR BETWEEN THE VARIOUS ELEMENTS OF L | BETWEEN P AND W OR INTEGRATED IN W (WOLLASTON EXAMPLE) OR BETWEEN W AND O | AFTER M | |
| CONFIGURATION 2 WITH ONE POLARIZER | BETWEEN M AND W | BETWEEN P AND W OR INTEGRATED IN W OR BETWEEN W AND O | NO | |
| CONFIGURATION 1 BIS | SAME AS CONFIGURATION 1 | NO | AN ADJUSTABLE ANALYZER A OR ONE SUITABLY ADJUSTED | BETWEEN P AND E |
| CONFIGURATION 2 BIS | | SAME AS CONFIGURATION 2 | NO | BETWEEN P AND E |

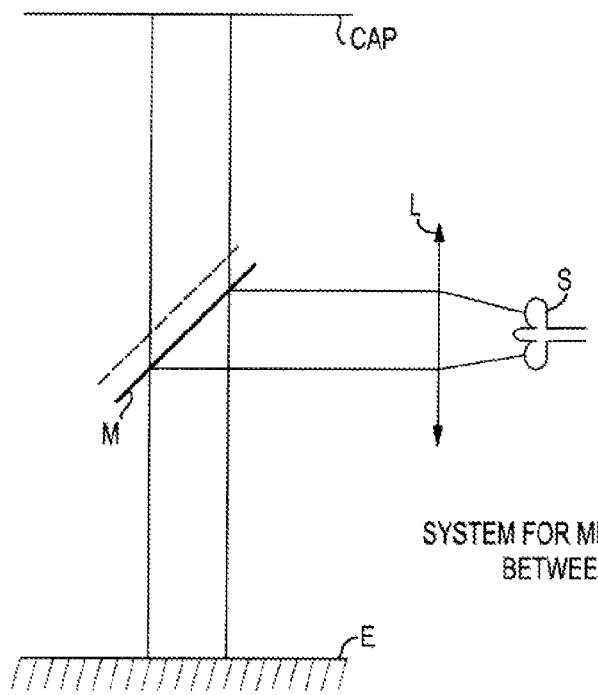
FIG. 12
SYSTEM FOR MEASUREMENT WITHOUT IMAGERY BETWEEN CROSSED POLARIZERS
FIG. 13A
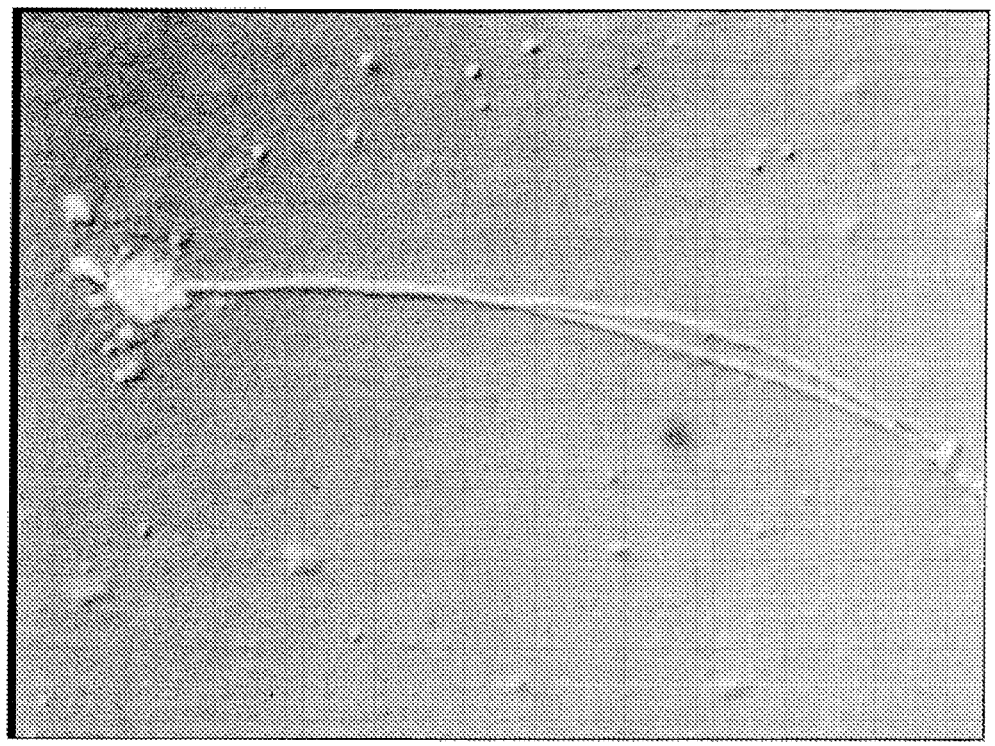

OPTICAL COMPONENT FOR OBSERVING A NANOMETRIC SAMPLE, SYSTEM COMPRISING SAME, ANALYSIS METHOD USING SAME, AND USES THEREOF

The present invention relates to the field of observation and analysis of nanometric characteristics using an optical component and a polarised light observation system.

Known in the state of the art is the technology that consists of preparing a sample support plate having index layers that meet specific conditions, such as provided in patents FR2818376 and FR2841339.

Also known in the state of the art is U.S. Pat. No. 5,631,171, describing equipment for observing nanometric thickness differences, by analysing the refraction of thin layers.

These various solutions require the design and production of a specific plate for each type of sample to be observed, and do not make it possible to conduct studies of undetermined samples or those with variable characteristics.

The present invention aims to solve these disadvantages by providing a solution that makes it possible to develop a broad range of applications for studying samples in which certain characteristics are not known, by observing their optical and physical characteristics.

The invention relates, according to its most general sense, to an optical component for observing a sample, comprising a substrate and at least one complex index layer of predetermined thickness, designed to show a high intensity or colour contrast for optical path variations, reliefs, nanometric thicknesses and diameters when it is observed by incoherent light reflection convergent around the normal incidence under polarisation extinction conditions, characterised in that the upper index layer has specific surface properties providing it with selective affinity relative to at least one characteristic of the sample.

Said optical properties are the natural properties of the upper index layer or are obtained by physical, chemical, physical-chemical, biochemical and biological modifications of the index layer.

We must therefore consider a pre-existing upper index layer and a subsequent functional modification that constitutes, in the majority of cases, an additional layer. The initial stacking is designed to become optically effective after the functional modification of the surface and/or in order for the desired optical situation to result from the association of a pre-stacking and the functional layer.

In the sense of the present patent, "sample" shall be understood to refer to an object in which certain characteristics are not known and are discovered by direct observation of very slight (nanometric) optical path variations, the lateral extension of which can also be very slight (nanometric), the adjective nanometric meaning that these lengths can be reasonably measured in nanometers. In the sense of the present patent, "optical component" shall be understood to refer to an association of a substrate and at least one complex index layer of predetermined thickness having affinity variations.

"Affinity" is understood to refer to the capacity of the surface of the component to combine with an external agent having determined and known physical, chemical or biological characteristics.

In the sense of the present patent, "affinity variation" is understood to refer to the fact that the surface has affine areas that correspond to non-constant physical, chemical or biological characteristics.

In the sense of the present patent, "affine area" is understood to refer to a surface area having specific affinity, which is different to the affinity of the surrounding areas.

The component according to the invention makes it possible to deduce from optical observation the characteristics corresponding to the affinity with all or part of the surface of the optical component containing the sample.

Advantageously:
said sample is observed under differential interference contrast,
said surface properties have affinity characteristics that vary according to the coordinates on the surface of the component,
the optical characteristics of the component vary according to the coordinates of the area being considered on the surface of the component,
the variations of the optical characteristics of the component and the variations of the surface properties are correlated,
said variations form a gradient following at least one direction of the optical component,
said variations are sudden, thereby delimiting clearly separate domains on the surface such as, for example, in the case of biochips, artificial noses, hydrophilic/hydrophobic boundaries or, in general terms, surface patterns.
said variations constitute even paving of the surface,
said variations constitute a matrix network,
the component has visible markers that make it possible to identify and locate a specific area.

According to the invention, the surface of the optical component has affinity properties that correspond to non-constant physical, chemical or biological characteristics. These affinity properties can consist of surface energy, surface electrical charge, surface polarisability, selective porosity, physical affinity, physical-chemical affinity, capture and/or recognition sites, liquid film, presence of a solution, magnetic agents, surface active agents, textures, chemical reaction cells, selective molecular traps, hydrophilic/hydrophobic patterns, millimetric, micrometric, nanometric patterns.

According to specific embodiments of the invention, the surface properties:
are the natural properties of the upper index layer,
are obtained in one or more steps by chemical reaction of components with the surface of the index layer by means of covalent chemical grafting or by electrostatic grafting of all charged molecular or macromolecular objects such as polyelectrolytes, electrolytes, proteins, dendrimers,
are obtained by physical modification of the index layer such as application of beamed particles or an electromagnetic beam; mechanical, acoustic, thermal, electric or magnetic action; erosion; selective deposition; plasma treatment; metallization; pressure variation; application of a liquid jet; deposition of ink, fumes, powder, layers in liquid form; solid contact,
are obtained by physical-chemical modification of the index layer in gas, liquid or solid phase such as inflation, deflation, dissolution, polymerisation, adsorption, wetting, capillarity, condensation, electrostatic effect, evaporation, crystallisation, deposition, electrodeposition, electrochemistry, electropolymerisation, demixing, self-assembly, dip-coating, spin-coating, microcontact printing, Langmuir-Blodgett transfer, in one or more steps by combining these modifications,
consist of a variation of the temperature or result from a variation of the temperature imposed on the sample,
consist of or result from lighting by means of an adjoining light beam,
consist of a variation of the pressure or result from a variation of the pressure, consist of a variation of the chemical nature of the surface, of the surface composition, of the surface roughness, of the surface altitude, of the reflection coefficient, of the surface potential such as an electric magnetic, electrostatic, zeta potential, a density of electric charges, a variable electrostatic charge valency, of a hydrostatic pressure, of an osmotic pressure, of linear or non-linear susceptibility (polarisability, light absorption coefficient, magnetic susceptibility, permeability, dielectric coefficient, Raman susceptibility, rotatory power, heat conduction, electric conduction, optical index, etc.), of a current density (electric, thermal, ionic, hydrodynamic, etc.), or consist of an anisotropy of any one of these properties, are obtained by applying an external field to the sample for all or part of the observation, including the thermal, luminous, electric, magnetic, electromagnetic, hydrodynamic and aerodynamic fields, and exposure to a beam or to a specific environment, are obtained by adding a biologically active layer or by biological or biochemical modification of the index layer or on the index layer by fixation using adsorption, grafting or depositing membrane structures in single-, double- or multi-layer form, pure or charged with membrane objects, by rupture of vesicles or liposomes or extracts of cellular membranes, by fixation of biological macromolecules, by direct fixation of proteins (for example, Bovine Serum Albumin) or by grafting of membrane amphipol-protein complexes, by fixation of ligands (for example by avidin-biotin associations), by fixation of antibodies or antigens, by fixation of cells, by lysis or by cell adhesion, by fixation of cellular components resulting from cell destruction, by fixation of chromatin and chromosomes in all their packing states, by direct fixation of chromosomes, by fixation of DNA or RNA, by molecular combing or by grafting or by incubation, by fixation of viruses or bacteria, by fixation of antiviral or antibacterial agents, by fixation of membrane receptors on a previously fixed bilayer, by fixation of polysaccharides, by fixation of cytoskeletons or cytoskeleton elements, by fixation of microtubules, of tubulin or myosin, by fixation of vegetable cell fibres, by fixation of chitin, by fixation of chitosan fibres, of cellulose fibres and by any combination of these various fixations, are obtained by depositing a layer of biologically active polymers, such as polyoside, polylysine, polypyrrole, polydimethylsiloxane, polyethylene glycol, are obtained by any combination whatsoever of various physical, chemical, physical-chemical, biochemical, biological operations, grant selective properties of intermolecular interactions that enable the selective and/or preferential fixation and/or recognition of interesting objects or of predefined objects such as proteins, peptides, amino-acids, antibodies, antigens, medicines, polysaccharides, lipids, liposomes, vesicles, toxins, metabolic products, synthesis molecules, aromatic molecules, fibres, filaments, DNA molecules, RNA molecules, chromosomes, cells, cellular extracts, bacteria, viruses, studs of a biochip, true and false hybrids of this environment, micellar structures, micromanipulation components, microfluidic components, organic complexes, inorganic complexes, organic-inorganic complexes, amoebae, fluorescent markers, steric markers, aggregates, clusters, condensates, drops of condensation, colloids, colloidal particles, metallic complexes, pollution agents, powders, fumes, gas, asbestos fibres, nanotubes, nanowires, nanoparticles, dendrimers, quantum dots, clay, leaves, organic vapours, zeoliths, salts, charged particles, counter-ions, solutions, surface active agents, catalysts, residue from chemical reactions, precipitates, crystals, in particular two-dimensional crystals, protein crystals and two-dimensional protein crystals, lipid crystals, mineral crystals, fat crystals, sugar crystals, polymer crystals, salt crystals or any combination of these various objects.

According to another embodiment of the invention, the association of said component with an observed sample constitutes an alternative or an element for coupling with the tracing of the samples using techniques such as radioactive labelling, spectroscopy, Raman spectroscopy, infrared, ultraviolet or visible spectroscopy, fluorescence, enzyme labelling, mass spectroscopy, piezoelectric detectors, amperometric detectors, surface sound wave detectors, surface plasmon resonance, profilometry, scanning probe microscopy, atomic force microscopy, ellipsometry.

According to other embodiments of the invention:
the optical component is fixed to the bottom of a Petri dish,
the substrate constitutes the bottom of a Petri dish.

The invention also relates to a sample analysis method using an optical component according to at least one of the preceding claims, characterised in that it comprises at least one step of placing the sample to be studied in contact with the selective affinity surface of said component, and at least one step of direct, real-time observation of the component thus prepared with equipment comprising an incoherent light source convergent around the normal incidence, and a system allowing the observation of the sample under polarised light and in extinction conditions, and optionally a step of storing the image thus observed.

According to a preferred embodiment:
the method comprises a system made up of a crossed polariser and analyser, placed on either side of the optical component along the useful path of the light,
the equipment comprises a polarisation separation device such as a Wollaston biprism or a Nomarski device and the sample is observed in differential interference contrast,
the device comprises a polychromatic, monochromatic, visible, partially visible or non-visible light source.

According to specific embodiments of the method of the invention, it comprises:
a step of identifying a specific area of the image using the markers that are visible on the component,
a step of analysing the colour and/or the intensity of the image according to the time and/or the positions along the surface and a comparison of these values with predetermined values,
a step of analysing the characteristics of the image, filtering the image according to a threshold of luminosity and/or a measurement of the position and intensity of the elements exceeding said threshold of luminosity according to the positions along the surface.

According to other variations:
it consists of analysing the intensity curve according to the wavelength of each point or part of the image for all the wavelengths present in the light spectrum, the equipment used must therefore comprise a spectrometer,
it consists of the intensity of a monochromatic image or of filtering or monochromatic projection of a colour image,
the method comprises a step of comparing, in the same conditions of observation, the colour and/or the intensity of the image according to time and/or to positions along the surface with those of a reference sample in which the characteristics are known, all or part of the establishment of contact is carried out by evaporation of the sample, all or part of the establishment of contact is carried out by immersion in a liquid phase and by stripping, the establishment of contact comprises at least one step of rinsing, incubation or drying, all or part of the establishment of contact is carried out by solid contact, for example by contact printing, the method furthermore comprises one or more steps of preparing the sample and/or a step of incubation and/or a step of immersion and/or a step of rinsing and/or a step of drying followed by a step of dry observation, the observations are carried out in immersion and the analysis consists of extracting the intensity or signal variations at every point in time, the establishment of contact and the observation are simultaneous, the establishment of contact is a hybridisation or adsorption or a chemical reaction of a solution with the component, and the mechanism is capable of being governed by Brownian diffusion or by convection, which is to say a given movement of the solution towards or along the surface caused by a hydrodynamic flow or an external field which can be electric, magnetic, thermal, luminous, etc.

Advantageously, the method comprises a step of detection and/or recognition and/or analysis using steric markers instead of fluorescent markers, said markers in turn being attached to an object that is capable of providing a function of recognition. This therefore results in two selective elements: the surface of the component which makes it possible to capture something and the element attached to the marker, which makes it possible to reveal or recognise what was captured. These steric markers have a diameter of less than 100 nanometers and, preferably less than 50 nanometers, preferably less than 10 nanometers and preferably less than 5 nanometers. The method according to the invention makes it possible to work with smaller steric markers than other techniques. The nature of these steric markers is arbitrary. These steric markers can, in turn, be equipped with a recognition site and can be used to analyse an unknown sample on the surface in a direct or indirect fashion.

According to another embodiment of the invention, the association of the component with an observed sample constitutes an alternative or an element for coupling with the tracing of samples using techniques such as radioactive labelling, spectroscopy, Raman spectroscopy, infrared, ultraviolet or visible spectroscopy, fluorescence, enzyme labelling, mass spectroscopy, piezoelectric detectors, amperometric detectors, surface sound wave detectors, surface plasmon resonance, profilometry, scanning probe microscopy, atomic force microscopy, ellipsometry.

According to a second variation, the association of the component with an observed sample constitutes an alternative to the tracing of samples using larger steric markers or those of an imposed nature.

According to another variation, the interaction of a target containing a steric marker and the observed sample constitutes an alternative to the tracing of samples using larger steric markers.

According to specific embodiments of the invention, the method comprises:

a step of selective and/or preferential fixation and/or recognition of interesting objects or of predefined objects such as proteins, peptides, amino-acids, antibodies, antigens, medicines, polysaccharides, lipids, liposomes, vesicles, toxins, metabolic products, synthesis molecules, aromatic molecules, fibres, filaments, DNA molecules, RNA molecules, chromosomes, cells, cellular extracts, bacteria, viruses, studs of a biochip, true and false hybrids of this environment, micellar structures, micromanipulation components, microfluidic components, organic complexes, inorganic complexes, organic-inorganic complexes, amoebae, fluorescent markers, steric markers, aggregates, clusters, condensates, drops of condensation, colloids, colloidal particles, metallic complexes, pollution agents, powders, fumes, gas, asbestos fibres, nanotubes, nanowires, nanoparticles, dendrimers, quantum dots, clay, leaves, organic vapours, zeoliths, salts, charged particles, counter-ions, solutions, surface active agents, catalysts, residue from chemical reactions, precipitates, crystals, in particular two-dimensional crystals, protein crystals and two-dimensional protein crystals, lipid crystals, mineral crystals, fat crystals, sugar crystals, polymer crystals, salt crystals or any combination of these various objects, a step of optical detection of any type of object associated with a single- or double-strand DNA molecule placed on or near a surface, a step of formation of nanometric or micrometric clusters on sites belonging to physical, chemical, physical-chemical or biological objects followed by a step of detection and/or observation of these structures.

It relates in this case to salt clusters whose formation depends on the process of incubation, stripping, rinsing and/or drying or to clusters of impurities or of biological agents such as proteins or other macromolecules, or of physical agents such as aggregates, or of chemical agents such as reagents or products of reactions or of impurities or of physical-chemical agents such as precipitates or the components of a mix, preferably absorbed, or of targets consisting of complementary steric objects such as metals or plastic, balls made from latex, gold or silicon attached to a ligand such as a single- or double-strand DNA molecule or an antibody or an antigen or a protein or a copolymer.

The step of forming physical-chemical clusters can be a step of forming liquid drops spontaneously in contact with their vapour. The step of formation of physical-chemical clusters is, for example, a step of forming water drops on the hydrophilic sites of a sample or of part of a sample, such as carbon nanotubes, a DNA molecule, a biological organism, a chromosome or a protein.

There are several optical configurations for implementing the method according to the invention:

the optical component containing the sample is placed along the optical path between a first optical system comprising a polariser and a second optical system comprising an analyser placed in an extinction position of the beam reflected by the component, the optical component containing the sample is placed along the optical path between a first optical system comprising a polariser and a quarter-wave plate and a second optical system comprising the same quarter-wave plate and an analyser, the optical component containing the sample is placed along the optical path between a first optical system comprising a polariser and a polarisation separating element such as a Wollaston biprism and a second optical system comprising the same polarisation separating element and an analyser, the optical component containing the sample is placed along the optical path between a first optical system comprising a polariser, a biprism and a compensator, and a second optical system comprising a compensator, a biprism and an analyser, at least one of the optical systems also comprises a quarter-wave plate, the analyser of the second optical system and the polariser of the first system constitute a single component, the separation between the two optical systems along the optical path, obtained by a semi-reflecting device, is located after the polariser of the first system along the optical path or before the polariser of the first system along the optical path, the analyser and the polariser then forming only one single element, the equipment for observing the sample comprises a lens, the optical component containing the sample is observed by reflection on the upper surface (microscope straight), the optical component containing the sample is observed by reflection on the lower surface (microscope inverted).

The invention finally relates to a sample analysis system comprising an observation device and an optical component containing a sample to be analysed, characterised in that said optical component is made up of a substrate and at least one complex index layer of predetermined thickness, designed to show a high intensity or colour contrast for nanometric thicknesses when it is observed by incoherent lighting reflection convergent around the normal incidence under polarisation extinction conditions, the upper index layer having specific surface properties providing it with selective affinity relative to at least one characteristic of the sample.

According to a preferred embodiment of the invention, this analysis system comprises a differential interference contrast device.

The observation device advantageously comprises:

a polychromatic or monochromatic light source, means of analysing the colour and/or the intensity of the image according to the time and/or the positions along the surface and a comparison of these values with predetermined values, means of analysing the characteristics of the image, filtering the image according to a threshold of luminosity and/or a measurement of the position and intensity of the elements exceeding said threshold of luminosity according to the positions along the surface, means of analysing the intensity curve according to the wavelength of each point or part of the image for all the wavelengths present in the light spectrum, means of analysing the intensity of a monochromatic image or filtering or monochromatic projection of a colour image, means of comparing, in the same conditions of observation, the colour and/or the intensity of the image according to time and/or to positions along the surface with those of a reference sample in which the characteristics are known, a reagent designed for preparing the sample with a view to placing it in contact with the selective affinity surface, a first optical system comprising said polariser and a second optical system comprising said analyser, a first optical system comprising said polariser and a second optical system comprising said analyser, each of said optical systems also comprising a biprism, a first optical system comprising said polariser and a second optical system comprising said analyser, at least one of said optical systems also comprising a compensator, a first optical system comprising said polariser and a second optical system comprising said analyser, at least one of said optical systems also comprising a lambda/4 plate.

The invention further relates to the following applications of the aforementioned method:

screening of crystals of proteins, peptides, lipids and any other molecule that is susceptible of forming crystals, screening of two-dimensional crystals instead of only three-dimensional crystals as is normal, studying intermolecular interactions, techniques for micromanipulation of viewed objects, reading and analysis of biochips with DNA, RNA, chromosomes, proteins, antigens, antibodies, cells, bacteria, viruses or any other type of chips, peptide analysis, studying membrane receptor multimerisation, studying axonal transport and the release of neurotransmitters, detecting and analysing chromosomes for the purpose of study or medical diagnosis using directly visible bands of colour or intensity on the chromosomes, analysing a single DNA molecule, non-destructive testing of liposomes, non-destructive testing of emulsions and/or suspensions, non-destructive testing of nanotubes, testing of fumes, testing of asbestos fibres, detection of traces, control of corrosion, control of land, air and water pollution, testing water quality, manufacturing sensors of gas, liquid, particles, "artificial noses", quality control of chemical grafting on solids, of layers, of various stages of depositing nanometric thicknesses, of Langmuir-Blodgett layers, quality control and manufacturing of microelectronic components, masks, micro-electro-mechanical systems (MEMS), supports for microelectronic and MEMS construction, recording media (CD and DVD), flat screens, following up the growth of layers and nano-objects, of nanotubes by CVD using a catalyst, checking and perfecting biocompatible surfaces, diagnosing membrane, tissue, cell extracts, studying and recognising polymer-membrane interactions, detecting birefringence, separation of phases, preferential adsorption, constructing molecular components, detecting and following up bacterial growth, cellular growth, controlling various steps of the enzymatic processes, controlling the nanometric growth of crystalline structures, quality control of sensitive layers for sensors during the manufacturing phase of the sensitive layer and/or during the development phase of the processes for implementing the sensor, said sensor being, for example, a biochip with DNA, RNA, chromosomes, proteins, antigens, antibodies, cells, bacteria, viruses, etc.

The invention will be understood better from reading the description of the non-limiting examples of embodiments thereof provided below, in reference to the appended drawings.

EXAMPLE 1

General Outline of the System for Analysis by Reflection

Figure 1:
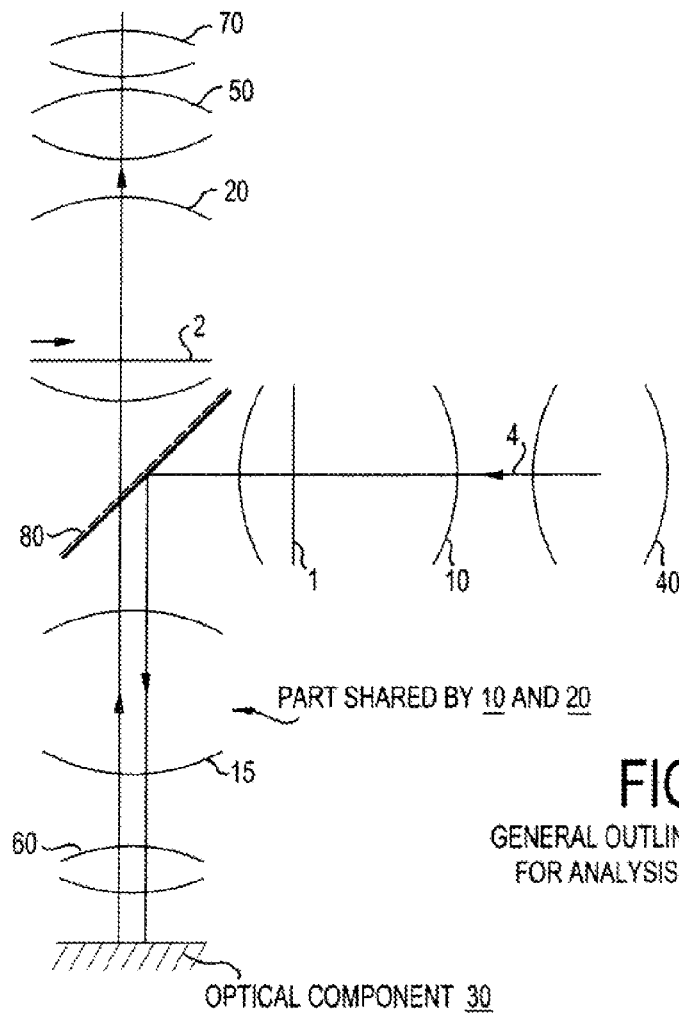

The analysis system shown in FIG. 1 comprises mainly the following:
- a first optical system (10) comprising a polariser (1)
- a second optical system (20) comprising an analyser (2)
- an optical component (30)
- a light source (40)
- a partially reflecting component (80)
- preferably a lens (60) for imagery
- preferably an eyepiece (50) for observation
- preferably an image-recording device (70)

It corresponds to a first embodiment of the invention designed for observation by reflection.

The two optical systems (10, 20) are disposed on either side of the optical component (30) in the path of the light. They can have a shared part (15).

The light source is a polychromatic source in the described example. This characteristic is not, however, limiting. The light source can be, for example, a halogen lamp, a xenon lamp, a mercury lamp, a sodium vapour lamp, an array of diodes, an incandescent lamp, a natural light source, a discharge lamp, or any other entirely or partially incoherent source.

The system (40) can comprise condensation and/or focusing optics, fibre optics, a diaphragm, or several elements as in the case of Köhler lighting. The image of the source is preferably focused on the rear focal plane of the lens (60). The lighting is preferably strong.

The beam of light (4) is polarised according to a first direction by the polariser (1). In the example of the chosen assembly, the direction of this polarisation is preferably perpendicular to the plane of the figure. The semi-transparent mirror (80) sends the polarised light to the sample.

Each point of the source lights the sample with a parallel beam of light having a different direction. The source is as wide as the beam of light is convergent. After reflecting off the sample, the beam of light returns on itself and passes back through the lens.

A part of this beam then passes through the semi-transparent mirror (80) to pass through the optical system (20), reduced in this example to an analyser (2) placed parallel to the plane of the figure.

A real image of the sample is finally obtained directly if the lens works at a finite distance or via a focussing lens if the lens works to infinity. This image is finally received by an eyepiece (not shown) for direct observation or captured by a camera (not shown) with a view to being stored.

EXAMPLE 2

Outline of an Optical Component According to the Invention

Figure 2A:
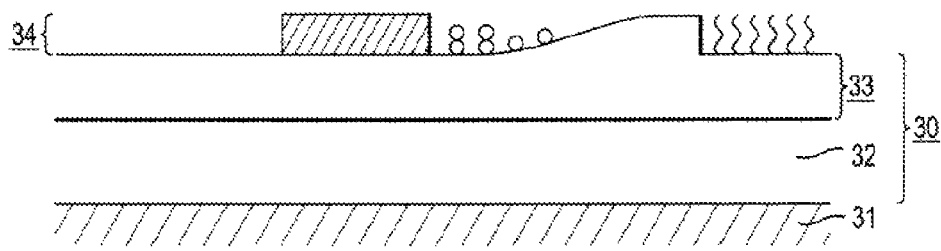
Figure 3:
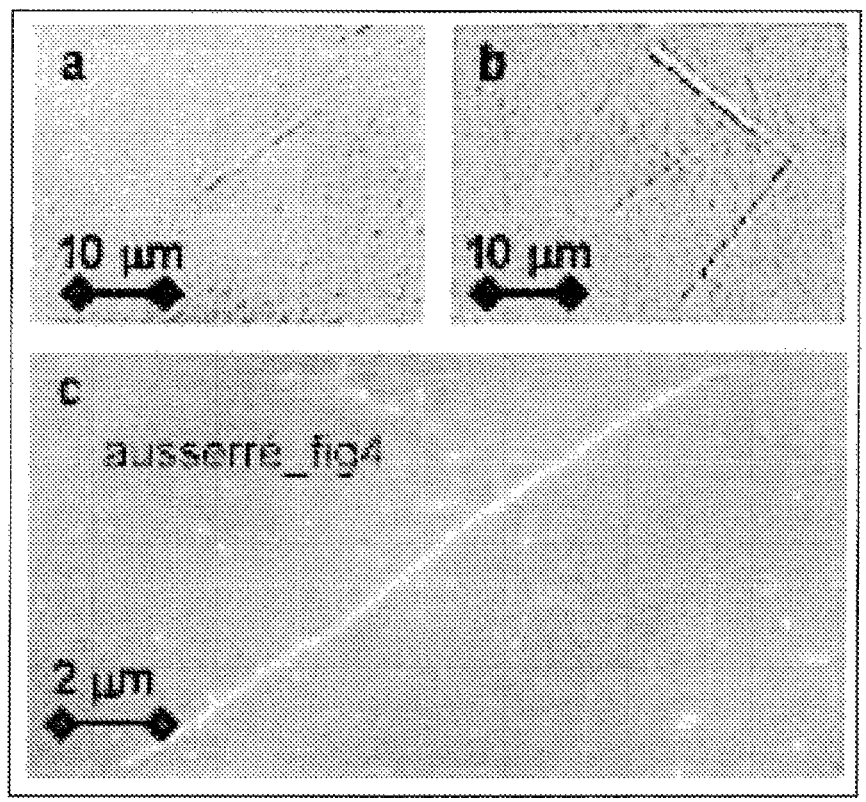
Figure 5:
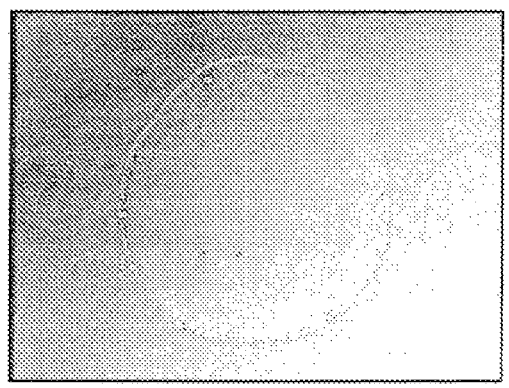

FIG. 2A describes an optical component used by the invention

The optical component (30) comprises a substrate (31) and has three main layers:
- a first index layer (32) having constant index and thickness characteristics over its entire surface
- a second index layer (33) having index and thickness characteristics that are adapted according to the associated application and affinity characteristics
- one or more selective affinity layers (34).

The two layers (33, 34) have characteristics which, for most applications, are not constant over the entire surface of the optical component.

The variations of the index characteristics of the layer (33) and of the affinity characteristics of the layer (34) are correlated such as to form on the component a plurality of partial zones having a determined pair of index and affinity characteristics.

These partial zones form, for example, a matrix made up of elements having a circular shape, each element corresponding to a specific index characteristic and an associated affinity characteristic which are different from those of the adjacent elements.

The optical observation of the optical behaviour of the sample on this component and, in particular, of the variations from one zone to another make it possible to deduce the physical-chemical or biological information of the observed sample.

FIG. 2B shows the various prototypes of optical components according to the invention.

EXAMPLE 3

Images of a DNA Strand Obtained Using the Optical Component According to the Invention These images show a double-strand lambda phage DNA molecule obtained by combing (very slow friction of the surface of the component using a solution with adjusted pH) on a component made up of a silicon support covered with a layer of silicon with a thickness of 104 nm (index layer) modified by a chemical treatment by HexaDiMethylSilizane (HDMS) in vapour phase. Part a shows an image obtained and recorded with an optical microscope (Leica DMRHC) equipped with episcopic lighting of a polariser and an analyser, an Apoplan X 100 lens, and working with interferential contrast. This image is the first unmarked image of a DNA molecule obtained using a never-published far-field optical technique. Part c shows the image of the same molecule reconstructed from scanning with an atomic force microscope (AFM) used as a reference technique.

The thickness of the molecule given by the device is 1.7 nm, which closely matches the theoretical diameter of the molecule, which is 2 nm. Part b shows a new image of the same molecule obtained using the same microscope after the study with the AFM. The nanometric defects introduced by AFM scanning draw a clearly visible square. Without previous optical marking, it is impossible to locate a given object as small as this molecule on a reasonably sized sample (larger than one square millimetre).

EXAMPLE 4

Figure 4:
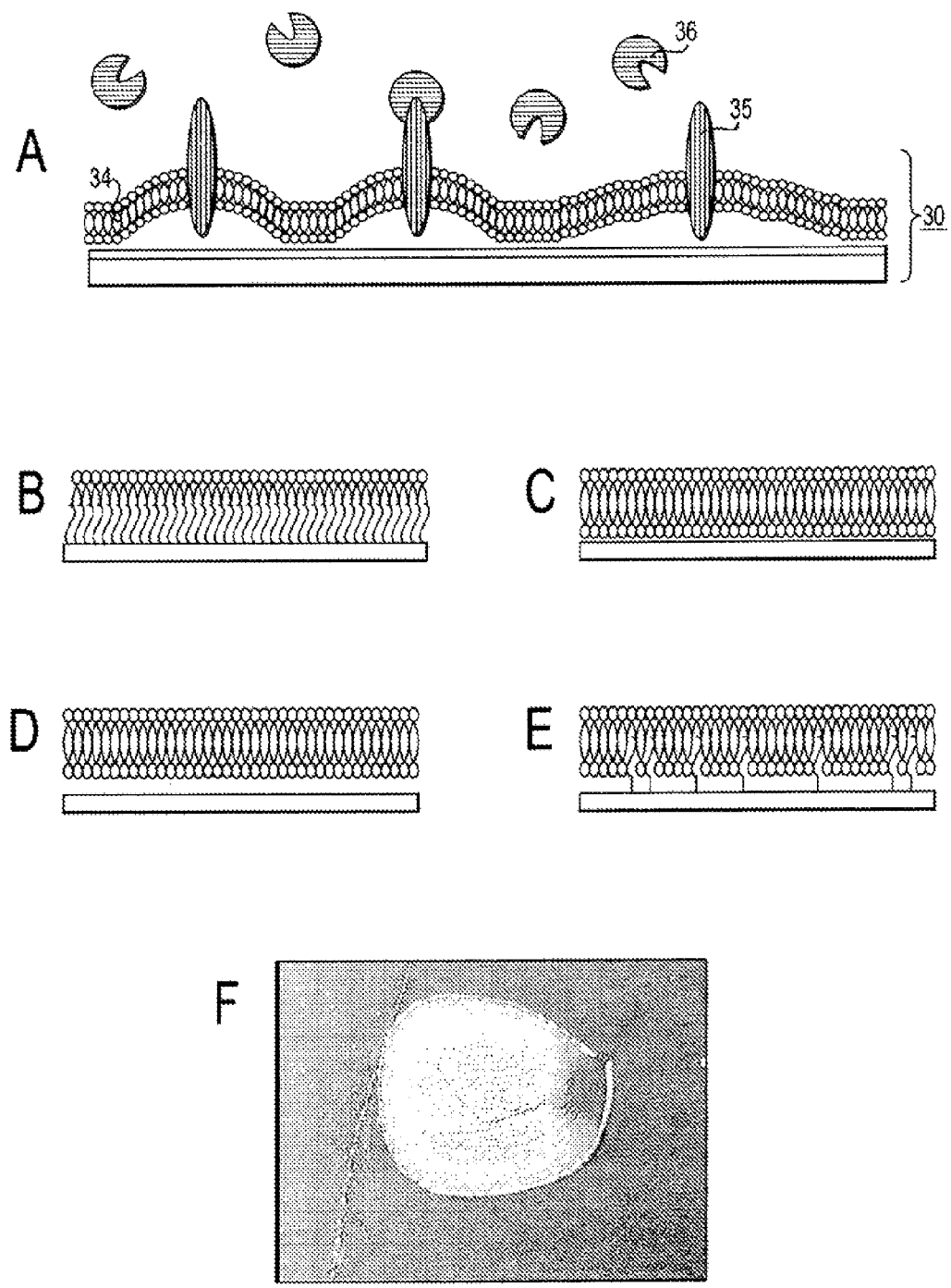

Overview of a Membrane Protein Sensor for Producing a Biochip with Membrane Proteins FIG. 4 shows an example of application for the production of a biochip with membrane proteins, designed for observation in the air for the purpose of analysing a mix.

The component (30) has a silicon substrate (31) and a layer with an index of 1.34 as well as selective affinity layers (34) consisting of studs with a thickness of 5 nm and irregular contours.

The index layer is a silica aerogel and has a thickness of 102.5 nm and a real index of 1.34.

Observation is carried out with a lens having a mean F number of 30 degrees.

The affinity layer (34) covering the surface is placed on an index layer (33) which can be formed from a highly hydrophobic self-assembled monolayer (FIG. 4B), a hydrophilic film (FIG. 4C), a cushion of polymer (FIG. 4D) or hybrid molecules grafted onto the surface (FIG. 4E). The studs have diameters of several dozen microns. These are discs made up of a membrane bilayer with a thickness of 5 nm which supports different receptors (35) for each stud, which are then capable of selectively quenching a ligand (36) present in an environment to be analysed.

In the described example, the biological material is made up of a lipid bilayer having membrane receptors (35) designed to sense a ligand (36). In contact with the environment, the studs each capture the complementary species of the receptor that they support.

Each stud captures a low or very low number of objects, which can be protein or peptide partners such as antibodies or hormones. The reading is carried out after rinsing by interferential contrast. Each object captured (nanometric) is displayed as a shiny point on a slightly luminous background. The objects can be easily counted.

In this example, the analysis method according to the invention is particularly advantageous compared with current fluorescence or ellipsometry techniques, since the signal it uses at one point of the image is generated by a very small surface around the captured object, typically the square of the lateral resolution of the observation system which corresponds to the smallest observable surface, or clearly less than one square micron, unlike fluorescence or ellipsometry techniques which use a signal generated by a much larger spot of light, larger than 100 square microns.

Since the useful signal in every case comes from the object and the noise or interfering signal in every case comes from the smallest observable region, the signal-to-noise ratio improves considerably when implementing the analysis method according to the invention.

The present invention therefore makes it possible to recognise the individual objects captured while the other techniques mentioned require the presence of a large number of identical objects in order to detect them. This constitutes an enormous advantage since the objects searched for in certain environments are very rare. Our technique is therefore preferable in every situation where the captured objects are of nanometric dimensions or are attached to objects of nanometric dimensions.

FIG. 4F shows a supported bilayer observed in the air.

EXAMPLE 5

Image of a Supported Bilayer Observed in Immersion

Image 5, which shows a supported bilayer observed in water, was obtained by immersion and in interferential contrast with support no. 15 (FIG. 2B).

The component (30) has a silicon substrate (31) and a layer with an index of 1.74 as well as selective affinity layers (34) consisting of studs with a thickness of 5 nm and irregular contours.

EXAMPLE 6

DNA Chips: Control and Reading

FIG. 6 shows images obtained using the analysis system according to the invention for DNA chips.

The surface of the component has a matrix of different types of affinity areas. Each area corresponds to a different affinity layer, comprising specific biological material. Such a component is placed in contact with a biological sample to be analysed.

Biochemical reactions take place between this sample and the biological material fixed to the various affinity areas of the component. The areas that brought about a biomolecular interaction have excess thicknesses of nanometric order and specific optical characteristics, in which observation using the system according to the invention leads to direct visualisation that makes it possible to deduce the biological nature of the sample.

Diagram 6A summarises the experiments conducted on the optical components according to the invention. The deposited DNA molecules are products of PCR with a length of 1000 base pairs. The biochips are prepared and revealed by means of a confidential method perfected by the Inserm U533 unit directed by Jean Léger.

At the end of the spotting process, observation of the supports (SP) shows that the spots are actually present. This first observation verifies that the work of the spotter was correctly performed. Image 6B shows that the spotter missed one deposit ($2^{nd}$ row, $4^{th}$ column).

Observations prior to hybridisation allow us to appreciate the quality of the deposits of PCR products. Image 6C shows that in this step it is possible to tell the deposits of solutions of PCR products from buffer deposits. A quick check of the spots makes it possible to ensure that they all have the same appearance, the same size and that they are homogeneous. Insufficiencies in the rinsing process leave residue that our technique can detect and qualify (manufacturing process control).

These observations also make it possible to appreciate the impact of the various treatments to prepare for hybridisation. The usefulness of saturation with bovine serum albumin (BSA) is also questioned in the observation of oligonucleotide deposits probed by our technique. By depositing on the surface, the BSA forms a layer with a thickness of 2-3 nm which reduces the height difference between the deposit and the bottom.

After hybridisation, the same deposits are always observed inside the same group on the various supports. The observed signals therefore come from the hybridisation step. The intensities and colours (the contrast) are thresholded so that the studs that capture DNA strands, or positive studs, appear covered with shiny points while the studs that do not capture anything, or negative studs, no longer appear (FIG. 6D).

Following the organisation of the deposits, none of the buffer deposits produced a signal. The observed signals therefore specify the presence of DNA.

The deposits observed by our technique (FIG. 6E) correspond to fluorescent deposits in microscopy (Image 6F) and under the scanner. And yet, this fluorescence is the consequence of hybridisation. That observed by our technique is therefore also the result of hybridisation.

In order to discover the quantity of hybridised material, the fluorescence signals after reading under the scanner are quantified. The signals for Cy3 and Cy5 are added up.

The results for a deposit group are reported in table 6G. A representation is provided in the form of a histogram (Graphic 6H), the position of each of the bars corresponding to that of the deposits, the height of the bars depending on the fluorescence signal level and their colour depending on detection by our technique.

In this group of deposits, there are a total of 72 deposits, of which 45 contain DNA and 27 only the buffer. The 27 buffer deposits are not detected by our technique with this contrast setting provided by the choice of component, in this case no. 7 (FIG. 2B). This was expected. Higher contrast can be obtained by using component no. 4 (FIG. 2B).

Among the 36 remaining spots of DNA solution, our technique makes it possible to view 27 in this configuration. The 9 that are not viewed correspond to 3 replicas of 3 different DNA solutions: R056X01A01, R056X01E05 and R056X01M05.

The deposited fragments have a standard size of 1000 pb, but these 3 solutions contain smaller fragments: R056X01A01->500 pb, R056X01E05->300 pb, R056X01M05->500 pb.

In short, using this component and this contrast setting, Sarfus makes it possible to view hybridisations with probes greater than 600 pb but not hybridisations with smaller probes.

The comparison of the images of the studs before and after hybridisation (images 6I and 6J) shows changes in their appearance due to the capture of DNA.

Image 6I shows that the differentiation between the stud and its environment is very large, that the defects of the stud and of the environment are clearly visible. This technique is therefore highly effective for checking manufacturing and incubation processes.

Image 6J, with its contrast reduced to ensure sufficient dynamism of the image, shows that the appearance of the hybridised stud is clearly different from that of the non-hybridised stud, the quenched DNA resulting in an excess thickness and introducing additional roughness.

This simultaneously illustrates the possibilities of optimising the processes of hybridisation, stripping, rinsing, drying, minimising unwanted adsorption and the possibilities of reading by differentiation of negative and positive studs. In addition, associated with techniques for thresholding or analysing intensity and/or colour, the technique is quantitative and makes it possible to assess the quantity of DNA captured on each stud.

This technique of reading chips without marking has a considerable advantage over fluorescence techniques in that the signal used is refractive in origin and therefore stable in time under lighting, unlike the fluorescence signal, which changes with the lighting time.

The technique also has the advantage of being compatible with very high-density chips, the minimum surface of a stud being around or less than one square micron.

EXAMPLE 7

Figure 7A:
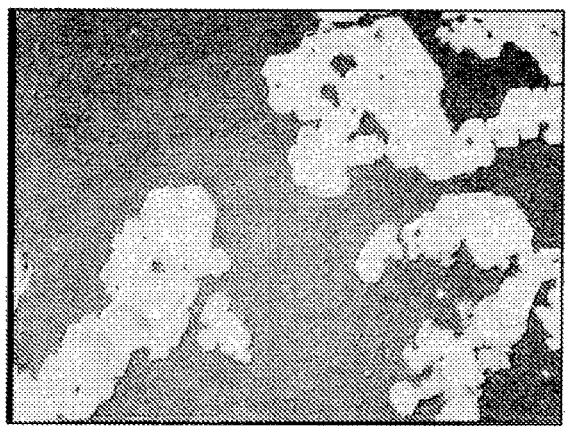

Use of the Optical Component According to the Invention for Detecting and Screening Two- and Three-Dimensional Crystals FIG. 7A shows two-dimensional protein crystals. The observed area has a length of 100 microns.

This figure shows the possibility of using the optical component according to the invention to detect protein crystals in a very early state (two-dimensional), which speeds up their detection, a considerable advantage for screening, and extends the search to proteins that form two-dimensional crystals but not three-dimensional crystals. It should be remembered that protein screening consists of identifying from among several candidates which ones crystallise, which makes it possible to study their structure by X-ray diffraction, stressing the fact that the X-ray diffusion techniques are applied to two-dimensional objects (GISAX technique, for example).

Figure 7B:
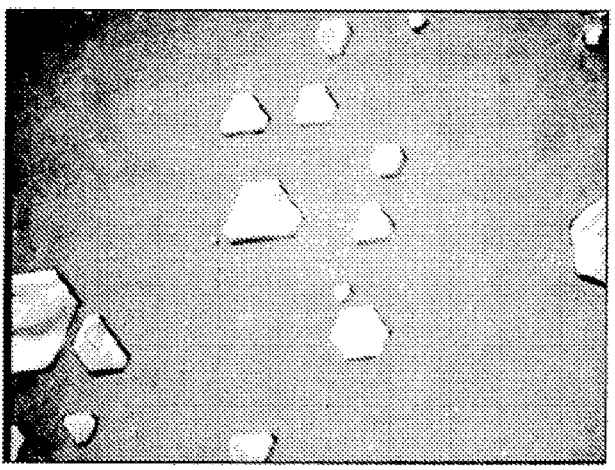

FIG. 7B shows the thin three-dimensional crystals of identical proteins obtained at a later stage. The image is 200 microns long. The surface of the component has been modified to make it hydrophilic, allowing the bovine serum albumin (BSA) present in the solution to deposit and crystallise when the solvent evaporates.

Figure 7C:

FIG. 7C shows 2D polymer crystals (Polyethylene Glycol 4000). The observed areas are respectively 100 microns and 200 microns long. The dendrites have a thickness of approximately 4 nm.

Figure 7D:
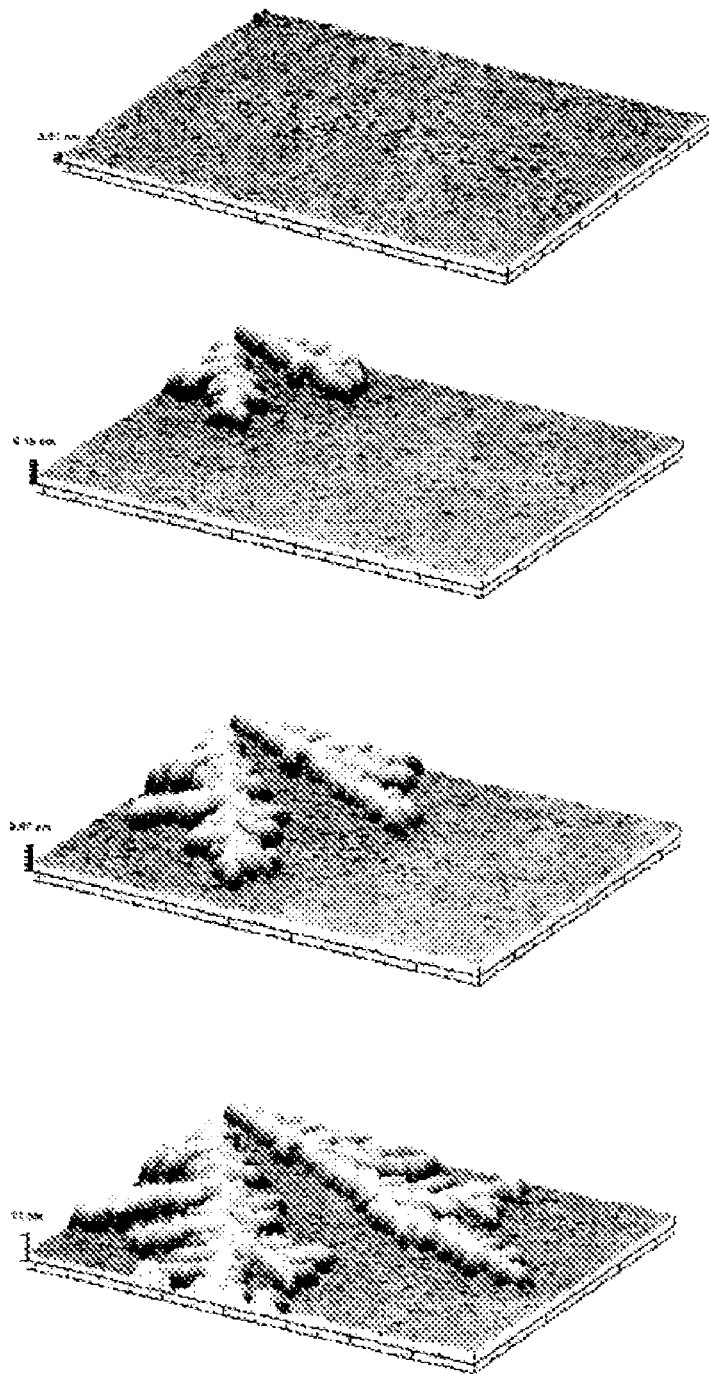

FIG. 7D shows the three-dimensional view of the crystallisation of this same polymer at room temperature. The images are 100 microns long. The formation of these dendrites on the surface is quick (around one micron per minute). This sequence of images shows the possibility of observing the kinetics of crystallisation at room temperature, which is inaccessible using other techniques.

It is possible here to see how the polymer crystallises from the amorphous polymer film. No other technique makes it possible to obtain this information.

EXAMPLE 8

Inspection, Control, and Follow-Up of the Crystallisation of a Protein Gel

Figure 8:
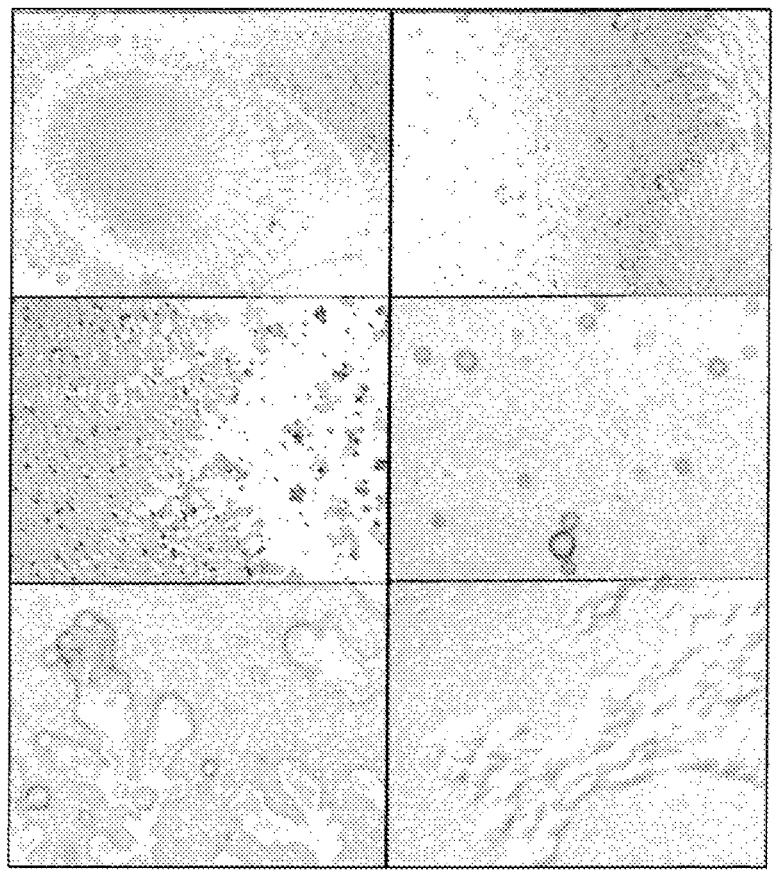

The large side of the six images in FIG. 8 is 200 microns. The first five are obtained dry between a crossed polariser and an analyser using component no. 7 (according to FIG. 2B).

The component used for the sixth image (bottom right) is a simple silicon support covered with a film of a solution in water with an approximate thickness of 100 nm, which can be checked with a device for checking segregation pressure, such as provided by Moldover and Cahn (Physical Review Letters, 1986). For the sixth image, the observation is conducted using differential interference contrast.

The samples are obtained from a solution of Beta-lactoglobulin (a milk protein) in water, used as it is (sixth image) or deposited on a surface activated by UV irradiation under oxygen (the other five images). This solution forms a gel whose growth is governed by the pH of the solution, checked during the experiment.

This example illustrates the possibility of following up, inspecting and controlling the processes of gelling and, more generally, of aggregation and crystallisation of proteins or other products, which is particularly advantageous in the agri-food sector, in particular for improving processes and checking production (texture of ice-cream, cheese, cream, yoghourt, etc.). It is also useful in the cosmetic sector, where a control of textures is equally important.

The observation method in this case is an alternative to confocal microscopy. The images show the structures formed at different times by the Beta-lactoglobulin in a solution (image 6 in FIG. 8) or after evaporation of a solution (other images in FIG. 8).

EXAMPLE 9

Application of the Optical Component According to the Invention for Studying and Inspecting Nanotubes FIG. 9A shows an image obtained with an example of the analysis system for studying and inspecting nanotubes. This image was obtained after CVD synthesis and shows an isolated multi-walled nanotube with the catalytic nanoparticle at one end.

There are different ways of synthesising nanotubes. According to the method and conditions chosen, different results are obtained, ranging from correctly aligned multi-walled nanotubes where they are linked to each other, to tangled or individual single-walled nanotubes. The residue from catalysis is added to these mixes.

The analysis method according to the invention makes it possible to categorise all these different types of nanotubes. Among these methods is CVD (chemical vapour deposition), which allows synthesis by growth on a surface from a catalyst nanoparticle or a nanometric defect.

It is important, in order to optimise and control this production, directly to follow up the growth of the nanotubes and the relative positions of the nanotubes and of the catalyst in each step of the process. The technique allows this. It is then necessary to work in the vacuum tank of the CVD device, which is possible considering the simplicity of our technique. A small interference microscope can be installed in the tank.

Another method of manufacturing nanotubes is laser ablation. Our technique makes it possible to view the result of this ablation on site.

Another manufacturing method is the electric arc method. This method is characterised by the great dispersity of the manufactured nanotubes. Our technique makes it possible to view and, at the same time, to sort certain nanotubes using an AFM.

For this purpose, the top surface must be free for micromanipulation. We therefore choose to work with a "rear surface" component on an inverse microscope. This component has the following characteristics: it consists of a floated glass substrate with a thickness of 1 millimetre, covered on one side only with a layer of chromium with a thickness of 5.3 nanometers and a layer of chromium dioxide ($CrO_2$) with a thickness of 6 nanometers.

The substrate is used in reflection on the covered surface and is attacked with light by the other surface. The useful surface is therefore observed through the glass.

It is advantageous to perform this observation immersed in oil in order to eliminate unwanted light coming from reflections on the surface of the glass.

According to the purpose of the observation, the surface can be used with its natural properties (high energy for direct deposition with strong anchoring of the tubes on the surface, for the purpose of inspection, counting or marking, for spectroscopic studies for example) or covered with a thin film of an amorphous polymer such as polydimethylsiloxane or even covered with a layer grafted by a chemical operation on the surface in vapour phase (for deposition by combing using a solution for micromanipulation operations).

FIG. 9B shows the detection of carbon nanotubes with rare shapes among interesting objects. This image, which has a length of 200 microns, was obtained by immersion and in interference contrast using support no. 16 (of FIG. 2B). It was then modified by silanisation using octadecyltrichlorosilane in toluene after UV+02 activation of the surface.

The nanotubes shown in FIG. 9B have been previously stabilised in an aqueous solution with SDS (sodium dodecyl sulphate) surface active agents. The interaction between the surface active agents and the silane layer is favourable for dispersed deposition of well-separated nanotubes.

EXAMPLE 10

Follow-Up of the Growth of a Bacterial Population

FIG. 10 shows an image with a length of 159 microns, which was obtained by immersion and by interference contrast with support no. 16 (of FIG. 2B), used with its natural surface properties. Indeed, it has considerable affinity for bacteria.

This component, associated with an interference contrast observation, makes it possible to follow up the growth of a bacterial population which develops on the surface.

The polymerised networks woven by the bacteria on the surface are not visible in this image due to the contrast settings, given by the choice of component, but can be visualised using component no. 13 (of FIG. 2B).

The bacteria are *Escherichia coli*. The method allows the detection of bacterial growth.

Components having specific affinity for bacteria allow excellent environmental control, in particular in the food sector.

EXAMPLE 11

Differential Contrast Device

FIG. 11A shows a differential contrast device according to the invention. A device for imaging a sample (E) in interference contrast by reflection comprises a light source (S); a lens (O); an imagery device of the light source next to the pupil of the lens (L); at least one polarising element (P, A); a polarisation separation element (W); a semi-transparent mirror (M).

It is also possible to add colour filters (FC) at any point between (S) and (OC) or (C). The mirror (M) can, in turn, be dichroic.

It can also comprise the following: a compensator element (C); a tube lens (LT); one or more eyepieces (OC); a camera (CAM); a lambda/4 retardation plate (L/4); another retardation plate (LR); a compensator (COMP). The element W introduces a lateral shift between two linear polarisations in a direction located at 45° with regard to the X and Y axes. This is, for example, a Wollaston biprism.

The camera or the ocular device are placed after (M). The possible tube lens is placed between (M) and (C) or (OE).

FIG. 11B shows different configurations of the differential contrast device.

EXAMPLE 12

System for Observation and Measurement Between Crossed Polarisers

A system for observing a sample (E) between crossed polarisers with no interference contrast is less restricting than the system described in the preceding example.

The system L is no longer essential.
The system W is absent.
All the rest of the preceding description remains valid.
FIG. 12 shows an imagery-free measurement system between crossed polarisers.

This system is a monosensor (the functional surface is homogeneous; there is no imagery).

It includes: a slightly convergent source (S+L); a sensor (CAP).

It has the advantage of being miniaturisable (example: source=light emitting diode; sensor=photovoltaic diode).

EXAMPLE 13

Interaction of a DNA Strand with Biological or Physical-Chemical Objects

FIG. 13A shows a rectangular area of the surface of the component with a length of 200 microns. The component is obtained by modifying the surface of component no. 7 (of FIG. 2B) using caesium hydroxide.

One drop of distilled water left to stagnate during several weeks is deposited on the thus modified surface. Cells (not identified) are viewed and deposited on the edge of the drop during the evaporation of the water, which also leaves a peripheral crown on the surface, which is attributed to positive and preferably divalent ions such as calcium.

The sample thus formed is subjected to a succession of alternating thermal shocks at −15° C. and +30° C. The cell ruptures and its chromatin is extracted.

Image 13A shows, on the left-hand side, the cellular residue. The sample is kept in a humid atmosphere. A part of the chromatin emerges gradually to the surface (towards the right) while another part remains packed and seems to form condensed chromosomes (to the left of the residue).

The stretched part corresponds to an unfolded chromosome with a thickness of around 30 nm. The two strands of the chromosome are clearly visible and are bound by a bridge (white stain shared by the strands towards the right of the image), which is clearly reminiscent of a centromere.

The association of the strands with biological objects, possibly histones or other large proteins, is clearly visible, as well as their affinity for a very thin film, which can be salt water or proteins around their point of separation.

In the region where the strands are separated, the symmetry of the patterns along the two strands is striking. These patterns reveal associations with other extremely small objects. This symmetry illustrates the specificity of the sites concerned by these associations and illustrates the possibility of using the method for diagnosis purposes.

The symmetry of their association with the thin film, which also covers the inter-strand space (adsorption), illustrates the possibility of testing or diagnosing a DNA molecule by means of physical-chemical agents.

Figure 13B:
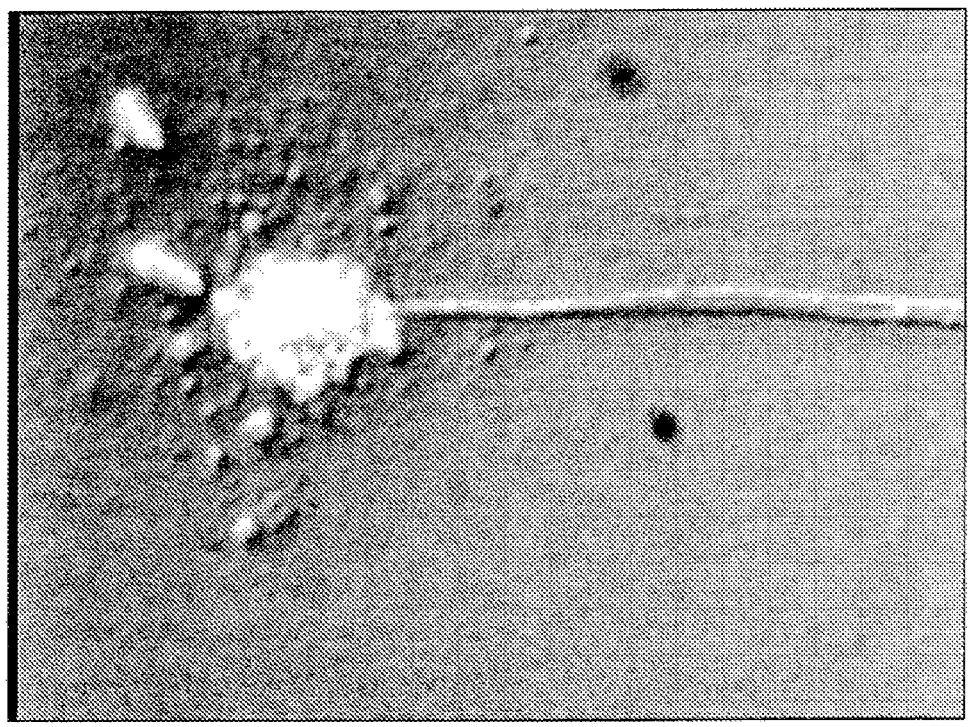

FIG. 13B shows the 100-micron long side of the preceding image, taken on the same system with greater magnification. This image shows the still-packed chromosomes more clearly. The shiny object located at the top has low-contrast coloured bands which allow it, in principle, to be identified.

Figure 13C:
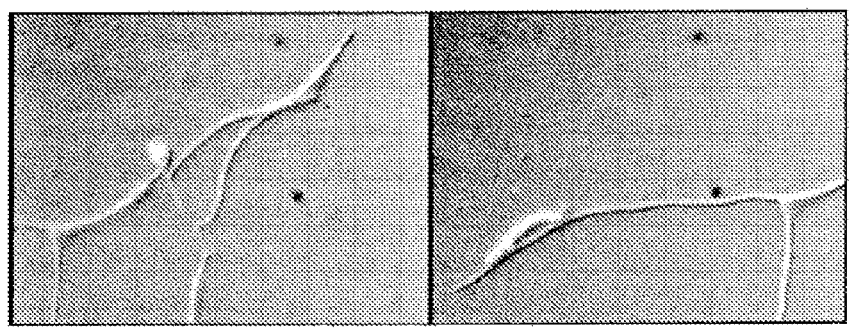

FIG. 13C shows the two images that have a length of 100 microns and are obtained in the same conditions as above. They illustrate the possibility of probing the interactions between partially unpacked DNA molecules (diameters between 10 and 30 nm according to brilliance) and varied biological objects (not identified here).

Figure 13D:
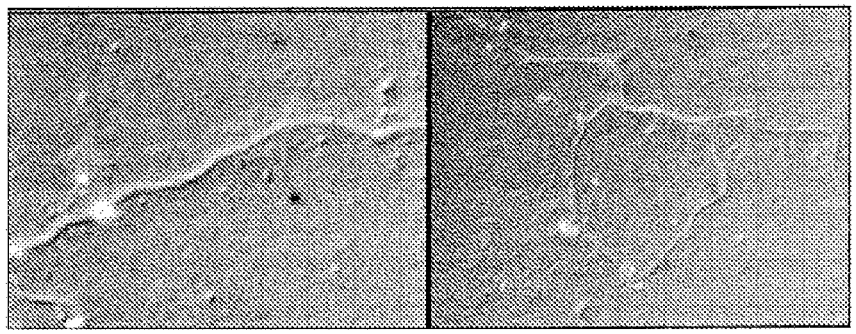

The two images of FIG. 13D show two unpacked DNA molecules obtained following the same method using a highly diluted solution of human saliva.

The interactions between this DNA taken from a single cell and varied biological objects are clearly visible.

The method allows genetic diagnoses to be made for the purpose of diagnosis or analysis, for example for sequencing. It has the enormous advantage of economising the PCR amplification and of allowing savings in terms of fluorescent markers, of being very easy to use and of providing much more accurate information: it is not only possible to find out what association takes place, but also where it takes place along the strand. For these reasons, the technique is an advantageous alternative to the FISH techniques (developed, for example, at the Pasteur Institute by Aaron Bensimon).

EXAMPLE 14

Figure 14A:
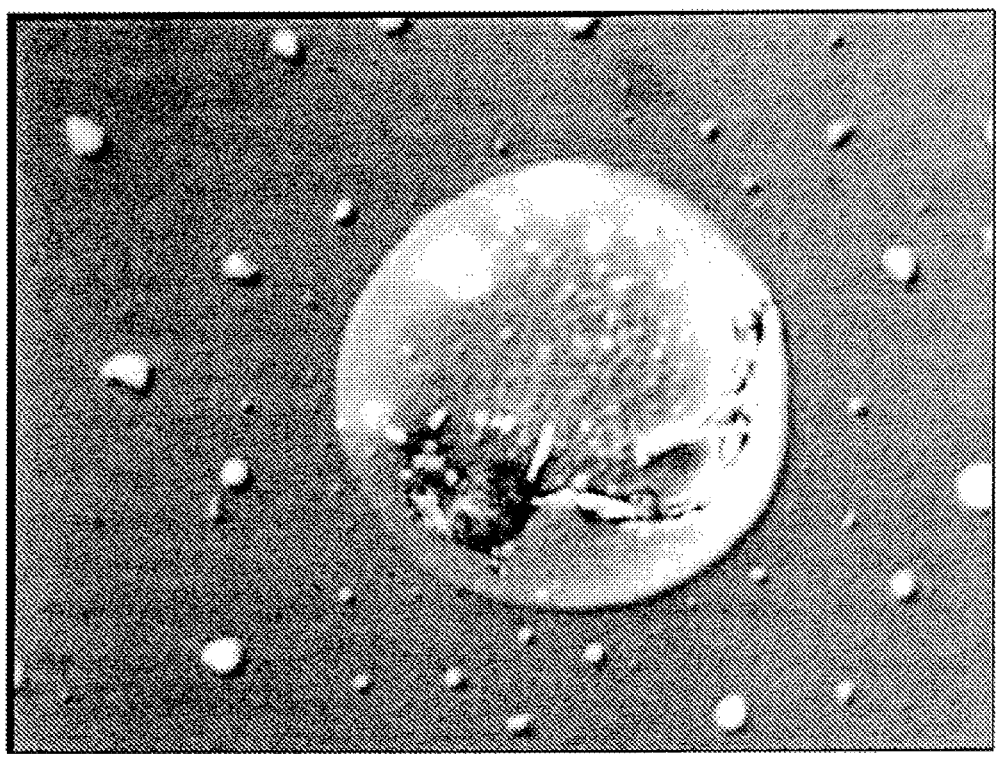
Figure 14B:
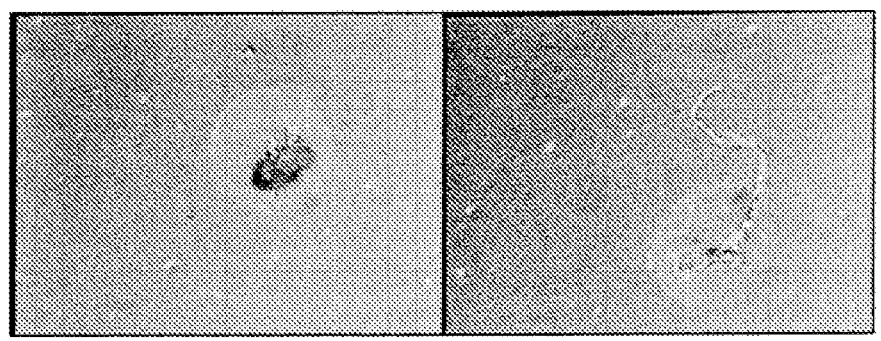
Figure 14C:
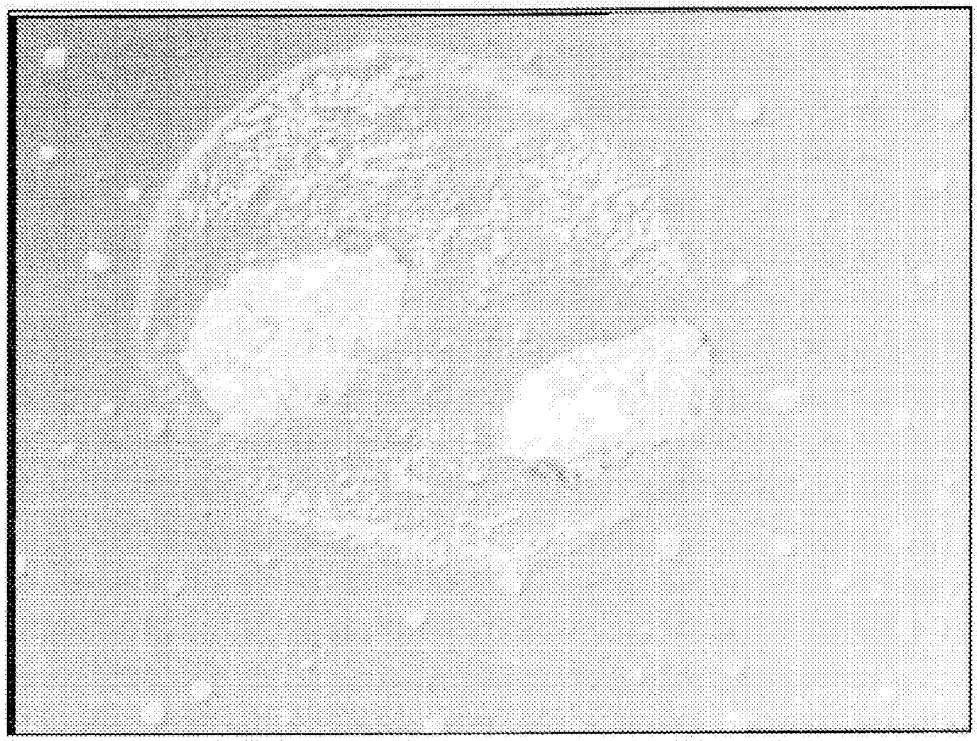
Figure 15A:
Figure 15B:
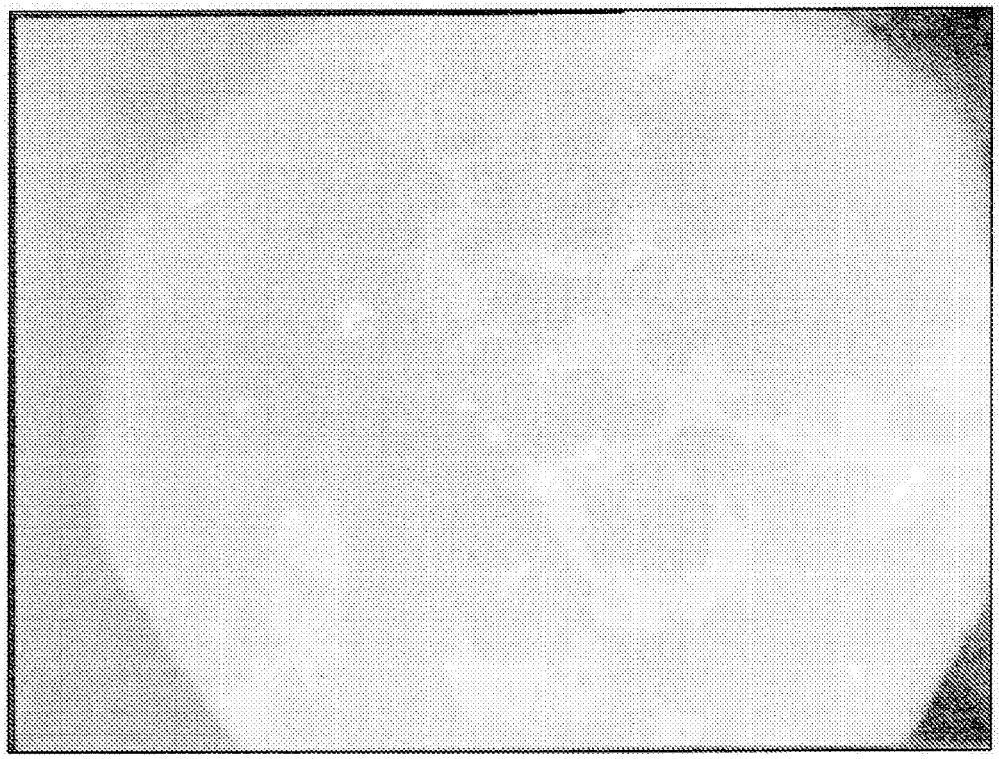

Diagnosis Method on a Cell Enabling the Identification of Receptors and Membrane Proteins Present in its Membrane This example is illustrated by FIGS. 14A, 14B and 14C. Image 14A has a length of 200 microns. The observation is made in interferential contrast. The component is component no. 7 (of FIG. 2B). Its surface is made hyper-hydrophilic by exposure to UV light coming from a discharge lamp with a strong component with a wavelength of 240 nanometers.

A highly diluted solution of human saliva is diluted in a glass of water (at an approximate ratio of 1 to 10,000) and one drop of this solution is deposited on the surface of the component. The eukaryote cells contained in the solution become strongly adhered to this surface and the cellular membrane, a bilayer in which the outer parts are hydrophilic, presses against the surface (clear disc) around the nucleus (coloured mass).

The evaporation of the water then increases the ionic force of the intracellular fluid and opens the walls of the nuclear membrane. The chromatin (coloured mass) is then extracted from the nucleus to take up the space between the two bilayers, still filled with fluid as can be seen by the brightening of the disc at its bottom right-hand side.

Numerous intracellular or membrane objects are visible on the rest of the disc, and all the membrane and transmembrane receptors are accessible for the purpose of diagnosis.

The method described in this example therefore enables all the operations that involve the ligands of these accessible objects. These ligands can directly detect or be themselves equipped with steric or fluorescent markers. The method allows the addressed receptors to be identified and located.

The two images in FIG. 14B show analogous cells obtained in the same conditions in an earlier stage (image on the left) and in a later stage (image on the right) of the process.

The sample corresponding to the image on the right was subjected to successive thermal shocks at −20° C. and +20° C. in a humid atmosphere, leading the chromatin to unpack on the surface.

Image 14C, obtained with the same settings, the same procedure and the same components as the preceding image, illustrates the usefulness of these observations for studying cellular mechanisms: in this case a cell in the anaphase stage of mitosis.

The two nuclei can be clearly seen (large objects on the left and right of the disc) and the masses of chromosomes (spread out at the ends of the equatorial plane). At the centre, traces of sleeves. The method allows the study of cellular mechanisms and the detection of functional or structural anomalies.

EXAMPLE 15

Observation of an Immersed DNA Solution

The present example is dedicated to the observation of a DNA solution immersed for the purpose of analysis and diagnosis. Image 15A, corresponding to an observed window with a total length of 159 microns, is obtained by interference contrast and by immersion. The solution is a rat brain DNA solution and the component is no. 15 (FIG. 2B).

The adsorption of the DNA on the Yttrium oxide resulting from deposition by CVD (chemical vapour deposition) is spontaneous. This DNA is associated in a solution with numerous biological objects with dimensions that range from several nanometers to several microns. These associations are revealed by the adsorption of DNA molecules on the surface, which appear as filaments associated with objects, in which the smallest, which have a diameter of several nanometers, appear to be spherical.

The association in a solution and visualisation by an adsorbent solution is an example of the diagnosis method that can be implemented using the component.

Image 15B of the same system is obtained after several hours of incubation and shows the associations of surface active agents contained in the initial solution with certain regions of the adsorbed molecules. Brownian diffusion mechanisms govern the kinetics of these associations, which can be speeded up by mechanical agitation or a hydrodynamic flow.

This example shows the possibility of performing tests based on physical-chemical associations in the interface between the component and a solution or solutions.

EXAMPLE 16

Examination and Recognition of Chromosomes, Direct Diagnosis of Chromosomes

The present example shows the application of the method according to the invention to the analysis of chromosomes. The images of FIG. 16 have a length of 100 microns. The image on the left was obtained by observation of the sample between a crossed polariser and analyser, and the image on the left is obtained by Nomarski's differential interference contrast.

Figure 16:
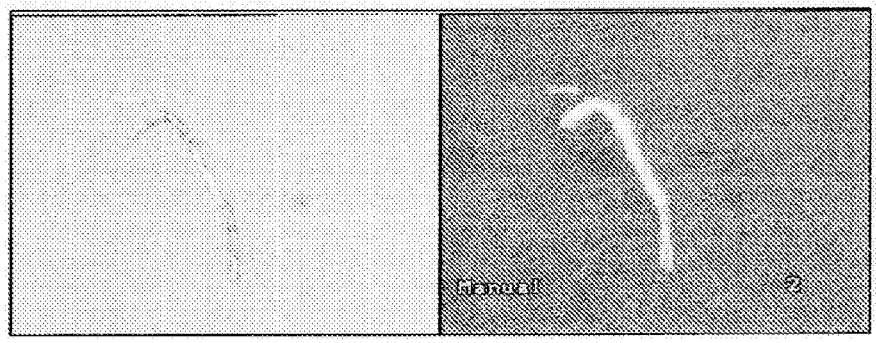

The two main objects visible in FIG. 16 are unfolded chromosomes probably taken from a cell in a pre-metaphase stage of mitosis.

One advantage of the analysis method according to the invention is that it does not require a specific mitotic phase to be blocked, since the objects extracted from the various cells are instantly recognised.

Direct analysis, for example for the purpose of diagnosis, is made possible by observation of the coloured bands that appear without marking and therefore without destruction of the objects. Another advantage is that a small number of cells is sufficient for implementing the observation.

Another advantage is that no filtering, blocking or replication process is required. The correct correspondence between the coloured bands and the bands obtained by standard marking processes has been verified. The chromosome is a human chromosome. The lighting lamp is a xenon lamp. The image on the left (FIG. 16) clearly shows the coloured bands and the image on the right shows the two strands of the chromosome and the centromere at the level of the fracture in the shape of the object.

EXAMPLE 17

Visualisation of Steric Markers

Figure 17:
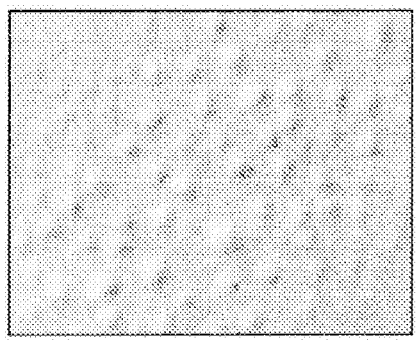

The image of FIG. 17, obtained by differential interference contrast, has a length of 15 microns and shows a population of colloidal gold balls, most of which have a diameter of 20 nanometers, deposited on component no. 7 (FIG. 2B) from a solution.

The component is made hydrophobic by depositing HDMS in vapour phase, which allows good dispersion of the deposited suspension by the movement of a drop on the surface with the help of a Pasteur pipette, a technique similar to combing which we practice.

In this method, the speed of the drop parallel to the support is of the order of 1 millimetre per second. This experiment illustrates the ability of the analysis method to visualise steric markers with very small dimensions. Markers ten times smaller can even be viewed in the same way, using the same component.

EXAMPLE 18

Importance of the Affinity Properties of the Surface

Figure 18A:
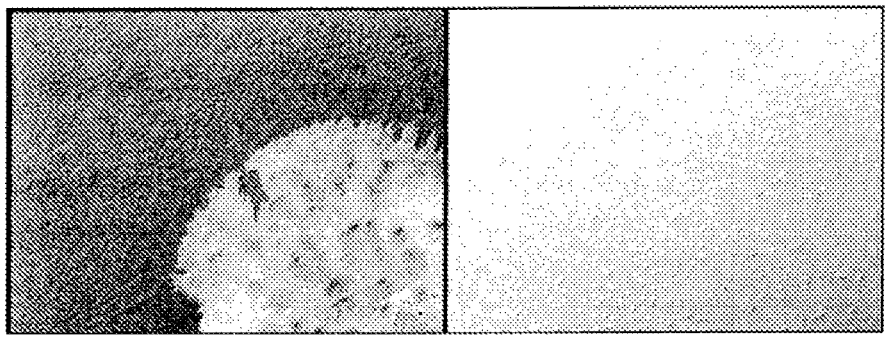
Figure 18B:
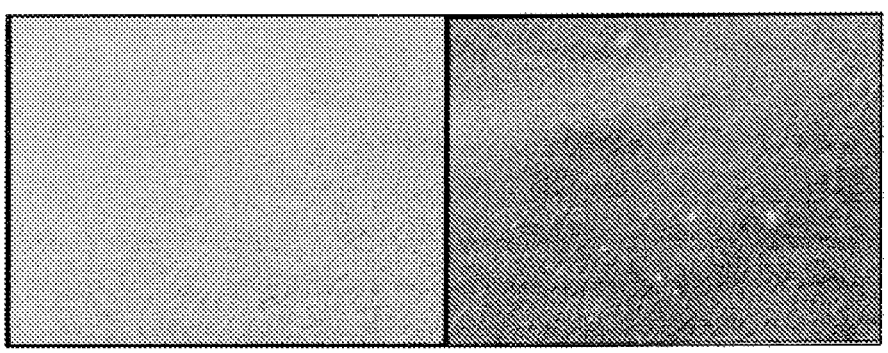
Figure 19:
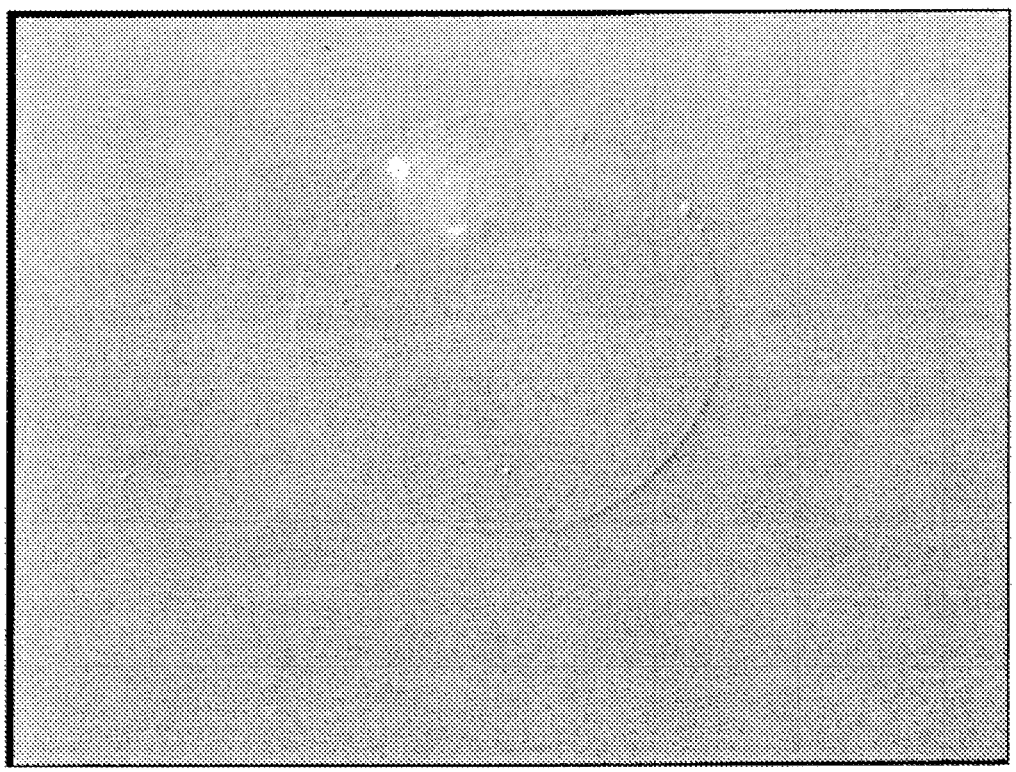
Figure 20A:
Figure 20B:
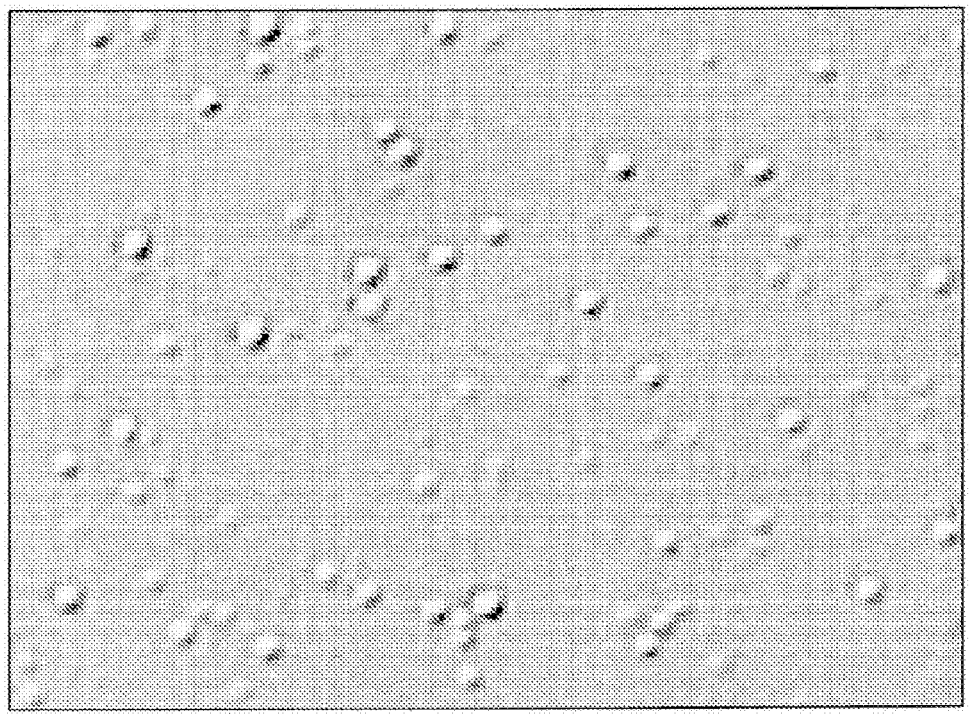

The two images of FIG. 18A, which have respective lengths of 200 microns (left) and 100 microns (right), show on component no. 7 (according to FIG. 2B) (on the left) and no. 7 modified by silanisation (on the right) the impact of the affinity of the surface on the structure of cationic surface active monolayers (SDS at 0.1%).

The surface active agents are deposited by evaporation from a solution highly diluted in distilled water. When the surface is hydrophobic (on the left), the layers are regular but either have holes in them (monolayer in the top left) or not (trilayer in the bottom right), suggesting chaotic positioning of the molecules, as in a liquid state.

When the surface is hydrophilic (on the right), the layers form faceted domains that reveal a crystalline order. Similar behaviour can be observed with anionic surface active agents such as HAC (hexadecyltrimethylammonium chloride at 5%).

As an example, image 18B on the left, taken in the same conditions, shows the crystalline structures obtained on the hydrophilic component.

However, we are in an intermediate case here, where the molecular order inside the layers is compatible with a full, regular structure of bilayers on several levels, as shown in the figure on the right in 18B, taken in the same conditions.

EXAMPLE 19

Phospholipidic Bilayers

Image 19, which has a length of 153 microns, shows a bilayer of phospholipids on a component no. 16 (FIG. 2B) after UV irradiation under oxygen.

The bilayer was obtained by depositing a very small amount of a solution of DPCC liposomes, a reference phospholipid. The deposition is carried out by direct contact (both solid and liquid) between a manual spotter with a diameter of 100 microns dipped in the solution and the component.

The observation is then carried out in the water by interference contrast. The observation shows the presence of a very regular bilayer (except at the top left) which is very stable in water. Such a bilayer can constitute a spot of a protein biochip.

The deposition technique is also compatible with the use of automatic spotters, and the bilayer can accommodate all kinds of receptors, previously introduced by mixing in the DPPC solution, the receptors then becoming integrated in the liposome bilayers. A different solution can be used for each spot, containing receptors determined after using the biochip.

EXAMPLE 20

Characterisation and Inspection of a Liposome Suspension

Liposomes are vesicles (sacs) in which the membrane is a bilayer of phospholipids. They are used for targeting active products in the cosmetic and pharmaceutical sectors, the sacs opening when in contact with the target.

It is important to study and inspect their behaviour when in contact with the target, which is characterised by its surface properties, the contact between the liposome and the target taking place on their surfaces.

The present invention allows this study and this inspection. The surface properties of the component must then reproduce those of the target.

It is also important to characterise the size distribution of the liposomes, since it can change with time and storage conditions.

For this purpose, it is possible to adjust the interaction between the liposomes and the surface of the component by adjusting its surface properties.

A favourable interaction leads:
either to the liposomes rupturing on the surface, each liposome becoming a puddle which can be a bilayer or a monolayer. This is particularly useful when the diameter d of the liposome is slightly less than the resolution r of the observation system, since the diameter of the puddle (disc) is twice that of the liposome (sphere).
For d>r/2, the puddle is resolved;
or to the formation of semi-liposomes on the surface. Each liposome appears in interference contrast as a point in which the light intensity and/or the colour depend on its diameter. The same proposal applies to "puddles" with a diameter of less than r/2.

The comparison with calibrated systems then makes it possible easily to characterise the distribution. In this application, the surface properties must be very homogeneous for the interaction of the liposomes with the surface to be entirely identical.

Image 20A has a length of 159 microns. The observation is made by interference contrast in immersion. The liposomes of unknown nature are objects from the cosmetics industry. The liposomes are spontaneously adsorbed on the component in which the surface is very homogeneous in the form of semi-liposomes, that is to say of hemispheres resting on the surface. The angle of contact of the objects on the surface is constant and very close to 90°. The shiny points correspond to objects with a diameter of 50 nanometers.

Enlargement of image 20B by a factor of around 10 shows how the size of the liposomes affects their appearance. The balls with a diameter barely smaller than 100 nanometers appear as very luminous stains with an apparent diameter that is comparable with the resolution of the microscope used, which is to say around 300 nanometers. Another population of much smaller objects, with an approximate diameter of 10 nanometers, takes on the appearance of stains with a diameter that is comparable with that of the preceding stains, but with a considerably lower luminosity. The suspension is therefore essentially bidisperse.

The component allows a functional link to be established between the size of the objects and their appearance (calibration), and then to follow-up changes in the distribution of objects in the solution, with the storage conditions and duration, for example. This application is very advantageous since it allows direct, easy to implement characterisation of objects observed individually, while the available techniques, based on the distribution of light (scatterometry) only provide access to mean quantities for the entire population.

This method of study, characterisation and inspection also applies to foams. The same method applies to emulsions, microemulsions, micelles, tubules, microtubules and any self-assembled structures of surface active agents, such as, for example, diblock copolymers.

EXAMPLE 21

Method of Analysing an Object Located on or Near the Surface of a Liquid, or at the Interface Between Two Liquids, where One or More Index Layer(s) is(are) Made Up of Said Liquid(s)

Figure 21:
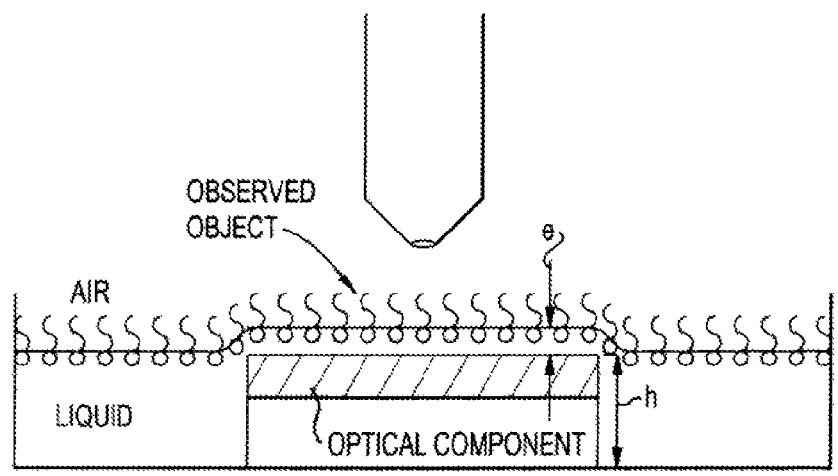

Observation of layers or objects located on or near the surface of a liquid (Langmuir layers, components adsorbed in the liquid/air interface) and follow-up of the interactions of these layers or these objects with external agents by means of an optical component according to the invention used in the assembly illustrated in FIG. 21.

The thickness e can be adjusted by means of the following device. A mechanical or piezoelectric device or the variation of the level of the Langmuir layer making it possible to place the optical component in a position h with a precision of the order of one nanometer.

The thickness e of the film results from a balance between segregation pressure and gravity. An adjustment of h makes it possible to adjust e with a precision of the order of several nanometers, such as to obtain maximum contrast.

According to a similar principle, it is possible to use a film of oil on the surface of the water, and to adjust the thickness of said film such as to obtain maximum contrast. Any other pair of non-miscible liquids can also be used.

The invention claimed is:

1. A sample analysis method using an optical component comprising:
providing an optical component for observing a sample, the component comprising a substrate and at least one complex index layer of predetermined thickness designed to show a high intensity or a colour contrast for optical path variations, reliefs, nanometric thicknesses and diameters when the index layer is observed by incoherent light reflection convergent around a normal incidence under a polarization extinction condition, wherein the upper index layer has specific surface properties providing it with selective affinity relative to at least one characteristic of the sample, and wherein the optical component produces a signal only when said component is combined with an external agent and otherwise produces no signal;
placing the sample to be studied in contact with the selective affinity surface of the component;
directly and in real-time observing the component thus prepared with an incoherent light source convergent around the normal incidence, thereby allowing the observation of the sample under polarised light and in extinction conditions; and
optionally storing the image thus observed.

2. A sample analysis method according to claim 1, wherein the observing step is performed using a system comprising a crossed polariser and an analyser placed on either side of the optical component along the useful path of the light.

3. A sample analysis method according to 2, wherein a separation between the two optical systems along the optical path is obtained by a semi-reflecting device.

4. A sample analysis method according to claim 3, wherein the separation is located after the polariser of the first system along the optical path.

5. A sample analysis method according to claim 3, wherein the separation is located before the polariser of the first system along the optical path, the analyser and the polariser then forming only one single element.

6. A sample analysis method according to claim 1, wherein the observing step is performed using a system comprising a polarisation separation device such as a Wollaston biprism or a Nomarski device, and wherein the sample is observed in differential interference contrast.

7. A sample analysis method according to claim 1, wherein the observing step is performed using a system comprising a polychromatic light source.

8. A sample analysis method according to claim 1, wherein the observing step is performed using a system comprising a monochromatic light source.

9. A sample analysis method according to claim 1, wherein the observing step is performed using a system comprising a visible light source.

10. A sample analysis method according to claim 1, wherein the observing step is performed using a system comprising a partially visible light source.

11. A sample analysis method according to claim 1, wherein the observing step is performed using a system comprising a non-visible light source.

12. A sample analysis method according to claim 1, further comprising the step of identifying a specific area of the image using at least one marker that is visible on the component.

13. A sample analysis method according to claim 1, further comprising the steps of:
analysing the colour or the intensity of the image according to a time or a position value along the surface; and
comparing the values to predetermined time or position values.

14. A sample analysis method according to claim 1, further comprising the steps of:
analyzing the characteristics of the image; and
filtering the image according to a threshold of luminosity or a measurement of the position and intensity of the elements exceeding the threshold of luminosity according to the positions along the surface.

15. A sample analysis method according to claim 14, wherein the analyzing step comprises analyzing the intensity curve according to the wavelength of each point or part of the image for all the wavelengths present in the light spectrum.

16. A sample analysis method according to claim 14, wherein the filtering step comprises filtering the intensity of a monochromatic image, or filtering a monochromatic projection of a colour image.

17. A sample analysis method according to claim 14, further comprising the step of comparing, in the same conditions of observation, the colour or the intensity of the image according to time or to positions along the surface with those of a reference sample in which the characteristics are known.

18. A sample analysis method according to claim 1, wherein all or part of the establishment of contact is carried out by evaporation of the sample.

19. A sample analysis method according to claim 1, wherein all or part of the establishment of contact is carried out by immersion in a liquid phase.

20. A sample analysis method according to claim 19, wherein all or part of the establishment of contact is carried out by stripping.

21. A sample analysis method according to claim 19, wherein the establishment of contact comprises at least one step of rinsing.

22. A sample analysis method according to claim 19, wherein the establishment of contact comprises at least one step of incubation.

23. A sample analysis method according to 1, wherein the establishment of contact also comprises a step of drying.

24. A sample analysis method according claim 1, wherein all or part of the establishment of contact is carried out by solid contact.

25. A sample analysis method according to claim 24, wherein all or part of the establishment of contact is carried out by contact printing.

26. A sample analysis method according to claim 1, further comprising:
preparing the sample by one or all of the steps of incubating, immersing, rinsing, and drying; and
dry observing the sample.

27. A sample analysis method according to claim 1, further comprising
detecting the sample using steric markers instead of fluorescent markers, said markers in turn being attached to an object that is capable of providing a function of recognition.

28. A sample analysis method according to claim 27, wherein the diameter of the steric markers is less than 100 nanometers, and preferably less than 50 nanometers.

29. A sample analysis method according to claim 1, wherein the association of the component with an observed sample constitutes an alternative or an element for coupling with the tracing of samples using techniques such as radioactive labeling, spectroscopy, Raman spectroscopy, infrared, ultraviolet or visible spectroscopy, fluorescence, enzyme labeling, mass spectroscopy, piezoelectric detectors, amperometric detectors, surface sound wave detectors, surface plasmon resonance, profilometry, scanning probe microscopy, atomic force microscopy, ellipsometry.

30. A sample analysis method according to claim 1, wherein the association of the component with an observed sample constitutes an alternative to the tracing of samples using larger steric markers or those of an imposed nature.

31. A sample analysis method according to claim 1, wherein the interaction of a target containing a steric marker and the observed sample constitutes an alternative to the tracing of samples using larger steric markers.

32. A sample analysis method according to claim 1, further comprising the step of selective or preferential fixation or recognition of interesting objects or of predefined objects such as proteins, peptides, amino-acids, antibodies, antigens, medicines, polysaccharides, lipids, liposomes, vesicles, toxins, metabolic products, synthesis molecules, aromatic molecules, fibres, filaments, DNA molecules, RNA molecules, chromosomes, cells, cellular extracts, bacteria, viruses, studs of a biochip, true and false hybrids of this environment, micellar structures, micromanipulation components, microfluidic components, organic complexes, inorganic complexes, organic-inorganic complexes, amoebae, fluorescent markers, steric markers, aggregates, clusters, condensates, drops of condensation, colloids, colloidal particles, metallic complexes, pollution agents, powders, fumes, gas, asbestos fibres, nanotubes, nanowires, nanoparticles, dendrimers, quantum dots, clay, leaves, organic vapours, zeoliths, salts, charged particles, counter-ions, solutions, surface active agents, catalysts, residue from chemical reactions, precipitates, crystals. In particular two-dimensional crystals, protein crystals and two-dimensional protein crystals, lipid crystals, mineral crystals, fat crystals, sugar crystals, polymer crystals, salt crystals or any combination of these various objects.

33. A sample analysis method according to claim 1, further comprising the step of detecting optically any type of object associated with a single- or double-strand DNA molecule placed on or near a surface.

34. A sample analysis method according to claim 1, further comprising the steps of:
forming nanometric or micrometric clusters on sites belonging to physical, chemical, physical-chemical or biological objects; and
detecting and/or observing the clusters.

35. A sample analysis method according to claim 34, wherein the clusters are salt clusters whose formation depends on the process of incubation, stripping, rinsing or drying.

36. A sample analysis method according to claim 34, wherein the clusters are impurities or biological agents such as proteins or other macromolecules, or physical agents such as aggregates, or chemical agents such as reagents or products of reactions, or impurities or of physical-chemical agents such as precipitates or the components of a mix, preferably absorbed, or targets consisting of complementary steric objects such as metals or plastic, balls made from latex, gold or silicon attached to a ligand such as a single- or double-strand DNA molecule or an antibody or an antigen or a protein or a copolymer.

37. A sample analysis method according to claim 34, wherein the step of forming physical-chemical clusters comprises forming liquid drops spontaneously in contact with their vapour.

38. A sample analysis method according to claim 34, wherein the step of forming physical-chemical clusters comprises forming water drops on a hydrophilic sites of a sample or of part of a sample, such as carbon nanotubes, a DNA molecule, a biological organism, a chromosome or a protein.

39. A sample analysis method according to claim 1, wherein the optical component containing the sample is placed along the optical path between a first optical system comprising a polariser and a second optical system comprising an analyser placed in an extinction position of the beam reflected by the component.

40. A sample analysis method according to claim 1, wherein the optical component containing the sample is placed along the optical path between a first optical system comprising a polariser and a quarter-wave plate and a second optical system comprising the same quarter-wave plate and an analyser.

41. A sample analysis method according to claim 1, wherein the optical component containing the sample is placed along the optical path between a first optical system comprising a polariser and a polarisation separating element such as a Wollaston biprism and a second optical system comprising the same polarisation separating element and an analyser.

42. A sample analysis method according to claim 41, wherein at least one of the optical systems also comprises a quarter-wave plate.

43. A sample analysis method according to claim 41, wherein the analyser of the second optical system and the polariser of the first system constitute one single component.

44. A sample analysis method according to claim 1, wherein the optical component containing the sample is placed along the optical path between a first optical system comprising a polariser, a biprism and a compensator, and a second optical system comprising a compensator, a biprism and an analyser.

45. A sample analysis method according to claim 1, wherein the system for observing the sample comprises a lens.

46. A sample analysis method according to claim 1, wherein the optical component containing the sample is observed by reflection on the upper surface with the microscope straight.

47. A sample analysis method according to claim 1, wherein the optical component containing the sample is observed by reflection on the lower surface with the microscope inverted.

48. An application of the method according to claim 1 to at least one of the following:
    detecting and screening of crystals of proteins, peptides, lipids and any other molecule that is susceptible of forming crystals;
    screening of two-dimensional crystals,
    studying intermolecular interactions;
    micromanipulating viewed objects;
    reading and analyzing biochips having one of DNA, RNA, chromosomes, proteins, antigens, antibodies, cells, bacteria, and viruses;
    analyzing peptides;
    analyzing membrane receptor multimerisation;
    analyzing axonal transport and the release of neurotransmitters;
    detecting and analysing chromosomes for the purpose of study or medical diagnosis using directly visible bands of colour or intensity on the chromosomes;
    analysing a single DNA molecule;
    non-destructively testing of liposomes;
    non-destructively testing of emulsions or suspensions;
    non-destructively testing of nanotubes;
    testing of fumes;
    testing of asbestos fibres;
    detection of traces;
    controlling of corrosion;
    controlling one of land, air and water pollution;
    testing water quality;
    manufacturing sensors of gas, liquid, particles,
    controlling quality relating to one of chemical grafting on solids, of layers, of various stages of depositing nanometric thicknesses, and of Langmuir-Blodgett layers;
    controlling quality of manufacturing of one of microelectronic components, masks, micro-electro-mechanical systems (MEMS), supports for microelectronic and MEMS construction, recording media (CD and DVD), and flat screens;
    monitoring the growth of one of layers and nano-objects, and of nanotubes by CVD using a catalyst;
    checking and perfecting biocompatible surfaces;
    diagnosing one of membrane, tissue, and cell extracts;
    studying and identifying polymer-membrane interactions;
    detecting one of birefringence, separation of phases, and preferential adsorption;
    constructing molecular components;
    detecting and monitoring bacterial growth or cellular growth;
    controlling various steps of an enzymatic processes;
    controlling the nanometric growth of crystalline structures; and
    controlling quality of sensitive layers for sensors during the manufacturing phase of the sensitive layer or during the development phase of the processes for implementing the sensor, the sensor being a biochip having one of DNA, RNA, chromosomes, proteins, antigens, antibodies, cells, bacteria, and viruses.

49. A sample analysis method comprising the step of:
    analyzing a sample,
    wherein the sample is analyzed using an observation device and an optical component containing the sample to be analysed, wherein the optical component comprises a substrate and at least one complex index layer of predetermined thickness designed to show a high intensity or colour contrast for nanometric thicknesses when it is observed by incoherent lighting reflection convergent around the normal incidence under polarisation extinction conditions, the upper index layer having specific surface properties providing it with selective affinity relative to at least one characteristic of the sample, wherein the optical component produces a signal only when said component is combined with an external agent and otherwise produces no signal.

50. A sample analysis method according to claim 49, further comprising analyzing the sample using a differential interference contrast device.

51. A sample analysis method according to claim 49, wherein the observation device comprises a polychromatic or monochromatic light source.

52. A sample analysis method according to claim 49, wherein the observation device comprises means for analysing the colour or the intensity of an image of the sample according to a time or a position along the surface and a comparison of the time or position values with predetermined values.

53. A sample analysis method according to claim 49, wherein the observation device comprises means for analysing the characteristics of an image of the sample by filtering the image according to a threshold of luminosity or a measurement of the position and intensity of the elements exceeding said threshold of luminosity according to the positions along the surface.

54. A sample analysis method according to claim 49, wherein the observation device comprises means for analysing an intensity curve according to the wavelength of each point or part of an image of the sample for all the wavelengths present in the light spectrum.

55. A sample analysis method according to claim 49, wherein the observation device comprises means for analysing the intensity of a monochromatic image or of filtering or monochromatic projection of a colour image of the sample.

56. A sample analysis method according to claim 49, wherein the observation device comprises means for comparing, in the same conditions of observation, the colour or the intensity of an image of the sample according to a time or a position along the surface with those of a reference sample in which the characteristics are known.

57. A sample analysis method according to claim 49, further comprising at least one reagent for preparing the sample to be in contact with the selective affinity surface.

58. A sample analysis method according to claim 49, further comprising a first optical system comprising the polariser; and a second optical system comprising the analyser.

59. A sample analysis method according to claim 49, further comprising a first optical system comprising the polariser; and a second optical system comprising the analyser, wherein each of the first and second optical systems also comprise a biprism.

60. A sample analysis method according to claim 49, further comprising a first optical system comprising the polariser; and a second optical system comprising the analyser, wherein at least one of the first and the second optical systems also comprises a compensator.

61. A sample analysis method according to claim 49, further comprising a first optical system comprising the polariser; and a second optical system comprising the analyser, wherein at least one of the first and the second optical systems also comprises a lambda/4 plate.

* * * * *